US012599723B2

(12) United States Patent
Hebert et al.

(10) Patent No.: US 12,599,723 B2
(45) Date of Patent: Apr. 14, 2026

(54) VIAL GEOMETRIES FOR OPTIMAL MIXING

(71) Applicant: BARD PERIPHERAL VASCULAR, INC., Franklin Lakes, NJ (US)

(72) Inventors: Casey Tyler Hebert, Loveland, CO (US); Amanda Thystrup, Phoenix, AZ (US); Brandon David Simmons, Tempe, AZ (US); Mark Nicholas Wright, Coventry, RI (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 677 days.

(21) Appl. No.: 18/003,055

(22) PCT Filed: Jun. 25, 2020

(86) PCT No.: PCT/US2020/039592
§ 371 (c)(1),
(2) Date: Dec. 22, 2022

(87) PCT Pub. No.: WO2021/262175
PCT Pub. Date: Dec. 30, 2021

(65) Prior Publication Data
US 2023/0270946 A1     Aug. 31, 2023

(51) Int. Cl.
*A61M 5/24*          (2006.01)
*A61J 1/14*          (2023.01)
(Continued)

(52) U.S. Cl.
CPC .......... *A61M 5/2448* (2013.01); *A61J 1/1406* (2013.01); *A61J 1/201* (2015.05);
(Continued)

(58) Field of Classification Search
CPC ........ A61J 1/2096; A61J 1/201; A61J 1/1406; A61J 1/01; A61J 1/20; A61J 1/2006;
(Continued)

(56) References Cited

U.S. PATENT DOCUMENTS 2,619,088 A    11/1952   Saffir
3,330,281 A     7/1967   Visser
(Continued)

FOREIGN PATENT DOCUMENTS

AU        2010310457 A1 *   5/2012    .............. A61J 1/201
CA          2655804 A1 *  12/2007    ................ A61J 3/00
(Continued)

OTHER PUBLICATIONS

Office Action dated Apr. 19, 2024 pertaining to CN 202080104414.2 filed Jan. 31, 2023.
(Continued)

*Primary Examiner* — Cris L. Rodriguez
(74) *Attorney, Agent, or Firm* — Dinsmore & Shohl LLP

(57)            ABSTRACT
A vial assembly includes a vial and a needle with at least one port. The vial includes a particulate material, a septum, a neck region including a first width, and a particulate region including a second width greater than the first width. The vial assembly is configured to move to a locked position. The needle may be configured to puncture the septum with the at least one port configured to be in the neck region when in the locked position. The at least one port may be configured to inject a fluid into the vial assembly to mix with the particulate material upon actuation of a vial engagement mechanism in a first direction and to receive a resulting mixed fluid from the vial assembly upon actuation of the vial engagement mechanism in a second direction opposite the first direction.

20 Claims, 25 Drawing Sheets

(51) Int. Cl.

| | |
|---|---|
| *A61J 1/20* | (2006.01) |
| *A61M 5/158* | (2006.01) |
| *A61N 5/10* | (2006.01) |

(52) U.S. Cl.
CPC ..... *A61M 5/158* (2013.01); *A61M 2205/3331* (2013.01); *A61N 5/1007* (2013.01); *A61N 2005/1021* (2013.01)

(58) Field of Classification Search
CPC .. A61M 5/1452; A61M 5/158; A61M 5/1458; A61M 5/1785; A61M 5/2005; A61M 5/2407; A61M 5/2448; A61M 2005/2403; A61M 5/285; A61M 5/2455; A61N 5/1007; A61N 2005/1021
See application file for complete search history.

(56) References Cited

U.S. PATENT DOCUMENTS

| | | | | |
|---|---|---|---|---|
| 4,122,836 | A * | 10/1978 | Burnett | A61M 5/1785 600/5 |
| 4,615,468 | A * | 10/1986 | Gay | A61M 5/1785 222/327 |
| 5,505,704 | A * | 4/1996 | Pawelka | A61M 5/31581 604/82 |
| 5,582,957 | A | 12/1996 | Sirianni et al. | |
| 5,695,480 | A * | 12/1997 | Evans | A61L 24/001 604/264 |
| 5,730,336 | A * | 3/1998 | Lerner | A45F 3/16 137/849 |
| 5,830,178 | A * | 11/1998 | Jones | A61K 47/6957 604/507 |
| 5,895,383 | A | 4/1999 | Niedospial, Jr. | |
| 5,957,166 | A * | 9/1999 | Safabash | B01F 35/712 141/2 |
| 6,499,617 | B1 | 12/2002 | Niedospial, Jr. et al. | |
| 6,544,236 | B1 * | 4/2003 | Cragg | A61B 17/0057 604/254 |
| 6,599,594 | B1 | 7/2003 | Walther et al. | |
| 6,874,760 | B2 * | 4/2005 | Steckel | F16K 15/147 251/342 |
| 6,984,222 | B1 | 1/2006 | Hitchins et al. | |
| 7,018,365 | B2 * | 3/2006 | Strauss | A61L 24/046 604/110 |
| 8,613,893 | B2 | 12/2013 | Ohashi et al. | |
| 8,652,423 | B2 | 2/2014 | Shick | |
| 9,327,886 | B2 | 5/2016 | Fazi et al. | |
| 9,381,135 | B2 * | 7/2016 | Reynolds | A61J 1/2096 |
| 9,642,774 | B2 | 5/2017 | Sattig | |
| 9,701,427 | B2 | 7/2017 | Algrain et al. | |
| 11,253,431 | B2 * | 2/2022 | Price | A61J 1/201 |

| | | | | |
|---|---|---|---|---|
| 11,744,775 | B2 * | 9/2023 | Chhikara | A61J 1/2075 604/411 |
| 2005/0159708 | A1 * | 7/2005 | Sidler | A61M 5/16877 700/282 |
| 2006/0106349 | A1 * | 5/2006 | Kito | A61M 5/344 604/199 |
| 2008/0033367 | A1 | 2/2008 | Haury et al. | |
| 2009/0182300 | A1 * | 7/2009 | Radmer | A61M 5/1409 604/411 |
| 2014/0231282 | A1 | 8/2014 | Young et al. | |
| 2014/0263319 | A1 | 9/2014 | Fazi et al. | |
| 2015/0045744 | A1 * | 2/2015 | Gupta | A61M 5/3134 604/241 |
| 2015/0290079 | A1 | 10/2015 | Nishioka et al. | |
| 2016/0206821 | A1 * | 7/2016 | Horiuchi | A61J 1/2096 |
| 2016/0265022 | A1 | 9/2016 | Yang-woytowitz et al. | |
| 2019/0381237 | A1 * | 12/2019 | Desbrosses | A61M 5/1409 |
| 2020/0100985 | A1 | 4/2020 | Auerbach | |
| 2020/0113784 | A1 | 4/2020 | Lopez et al. | |
| 2020/0163834 | A1 * | 5/2020 | Tashjian | A61J 1/2089 |
| 2020/0170884 | A1 * | 6/2020 | Tashjian | A61J 1/2089 |

FOREIGN PATENT DOCUMENTS

| | | | | |
|---|---|---|---|---|
| CN | 105026277 | B | 9/2017 | |
| DE | 202005020032 | U1 * | 2/2006 | A61M 16/0468 |
| JP | H0759865 | A | 3/1995 | |
| JP | 2002172151 | A | 6/2002 | |
| JP | 2004510461 | A * | 4/2004 | A61M 15/002 |
| JP | 2013524907 | A | 6/2013 | |
| WO | 9500244 | A1 | 1/1995 | |
| WO | WO-2011050333 | A1 * | 4/2011 | A61J 1/2055 |
| WO | 2011131781 | A1 | 10/2011 | |
| WO | WO-2012119225 | A1 * | 9/2012 | A61J 1/2096 |
| WO | 2015197546 | A1 | 12/2015 | |
| WO | WO-2019101645 | A1 * | 5/2019 | A61J 1/2065 |
| WO | 2019222713 | A1 | 11/2019 | |
| WO | WO-2019222699 | A1 * | 11/2019 | A61M 5/1566 |
| WO | 2020016165 | A1 | 1/2020 | |

OTHER PUBLICATIONS

JP Office Action dated May 7, 2024 pertaining to JP 2022-580324 filed Dec. 26, 2022.

Office Action dated Dec. 30, 2024 pertaining to CN application No. 202080104414.2.

Introduction to Packaging, Zeng Renxia, Hunan University Press, Dec. 31, 1989, pp. 146-151.

International Search Report and Written Opinion for PCT/US2020/0039592 mailed on Jun. 11, 2021.

Decision of Rejection dated Jan. 15, 2025 related to Japanese Patent Appln. No. 2022-580324 filed Dec. 26, 2025.

* cited by examiner

VIAL GEOMETRIES FOR OPTIMAL MIXING

CROSS-REFERENCE TO RELATED APPLICATIONS

This application is a U.S. national phase of International Application No. PCT/US2020/039592, filed Jun. 25, 2020, which is incorporated herein by reference in its entirety.

TECHNICAL FIELD

The present disclosure generally relates to components of medical devices for treating cancer, and more particularly to vial assembly components of medical devices configured and operable to deliver radioactive compounds to a treatment area within a patient's body in procedures such as transarterial radioembolization.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial Radioembolization is a transcatheter intra-arterial procedure performed by interventional radiology and is commonly employed for the treatment of malignant tumors. During this medical procedure, a microcatheter is navigated into a patient's liver where radioembolizing microspheres loaded with a radioactive compound, such as yttrium-90 ($^{90}$Y), are delivered to the targeted tumors. The microspheres embolize blood vessels that supply the tumors while also delivering radiation to kill tumor cells.

Generally, vial assembly components operate with syringes for manually administering the radioactive compound are prone to inconsistent flow rates and pressures from mixing in a vial permitting particulate to remain and settle and not be fully mixed with fluid in the vial. Such settling may require cleaning of the vial assembly components and/or connected components, which may cause insufficient injection rates and/or less efficient delivery resulting in decreased bead dispersion. Such decreased bead dispersion may impact efficacy of the treatment.

Accordingly, a need exists for vial assembly components of a medical device that is configured and operable to perform radioembolization that incorporates a simplistic design and consistent means for administering constant flow rates and pressure of the radioactive compound to the patient's body while preventing or reducing particulate settlement during such mixing and delivery.

SUMMARY

In accordance with an embodiment of the disclosure, a vial assembly may include a vial and a needle. The vial may include a particulate material, a septum, a neck region including a first width, and a particulate region including a second width greater than the first width. The needle may include at least one port. The vial assembly may be configured to move to a locked position, and the needle is configured to puncture the septum of the vial assembly when the vial assembly is in the locked position. The at least one port is further configured to be in the neck region of the vial assembly when the vial assembly is in the locked position. The at least one port is configured to inject a fluid into the vial assembly to mix with the particulate material upon actuation of a vial engagement mechanism in a first direction and to receive a resulting mixed fluid from the vial assembly upon actuation of the vial engagement mechanism in a second direction opposite the first direction.

In another embodiment, a vial may include a particulate material, a septum, a neck region, a particulate region, and an external wall. The neck region may include neck region a first width. The neck region may be a conical shape. The particulate region may include a second width greater than the first width. The external wall may include an external wall width, a particulate region thickness between the external wall and the particulate region, and a neck region thickness between the external wall and the neck region. The neck region thickness may be greater than the particulate region thickness.

These and additional features provided by the embodiments described herein will be more fully understood in view of the following detailed description, in conjunction with the drawings.

3

Figures 11A, 11B:
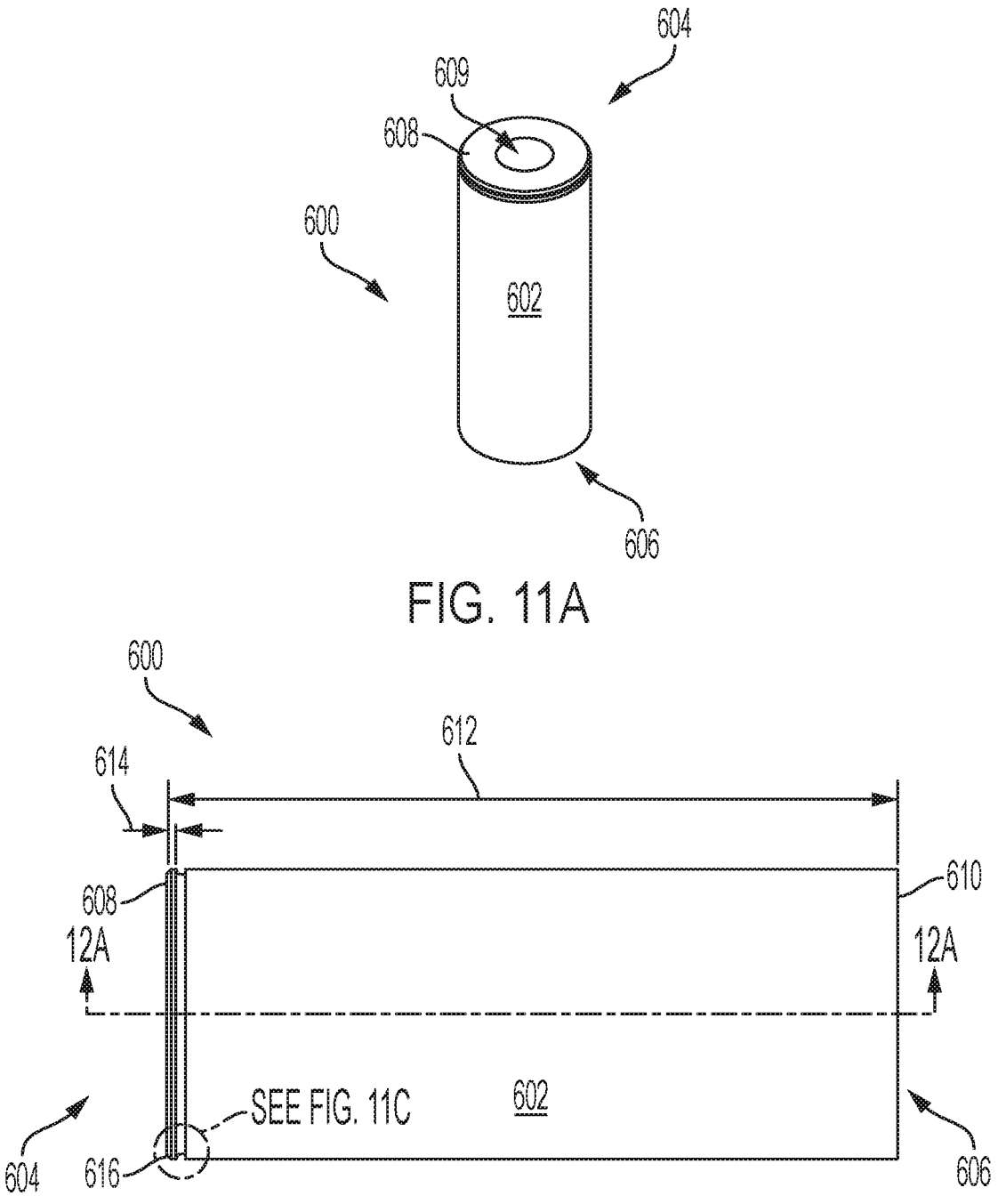
Figure 11C:
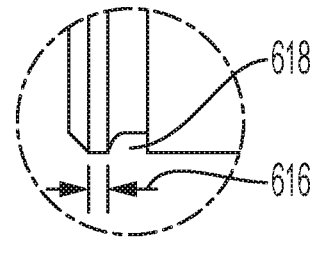
Figure 11D:
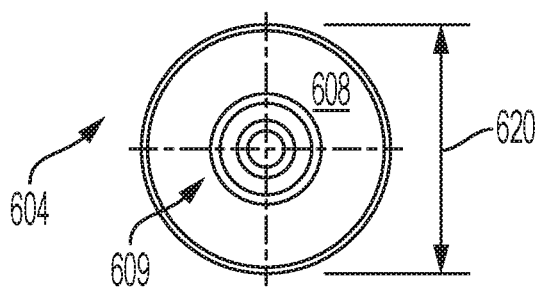
Figures 12A, 12B:
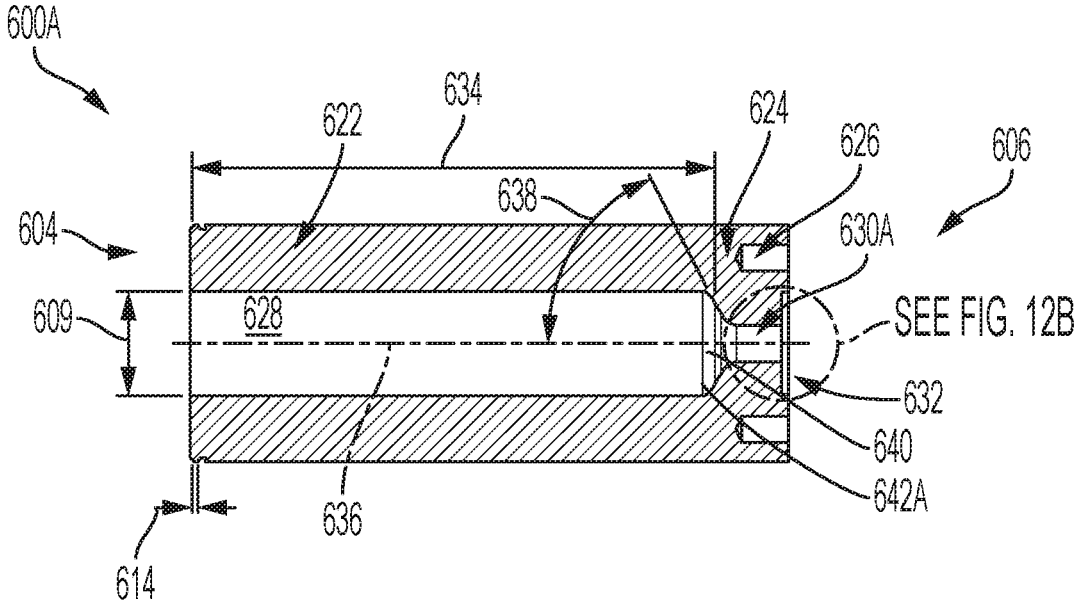
Figure 12C:
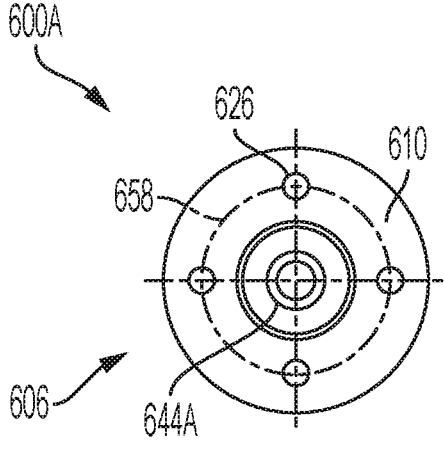
Figure 12D:
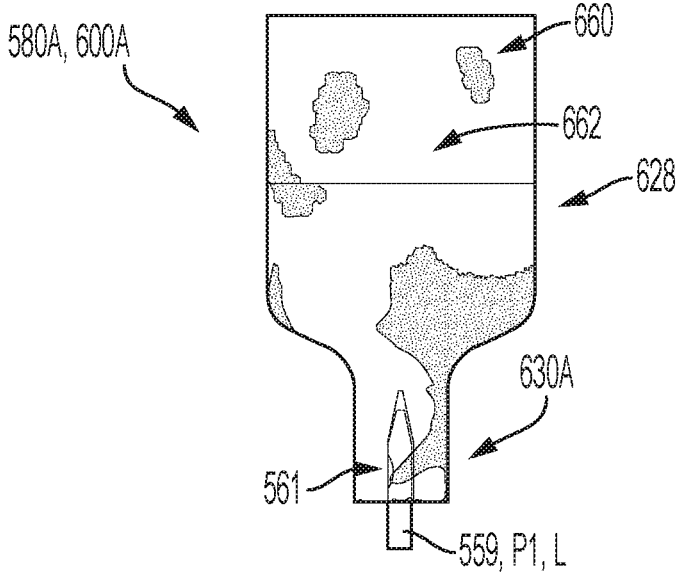
Figure 12E:
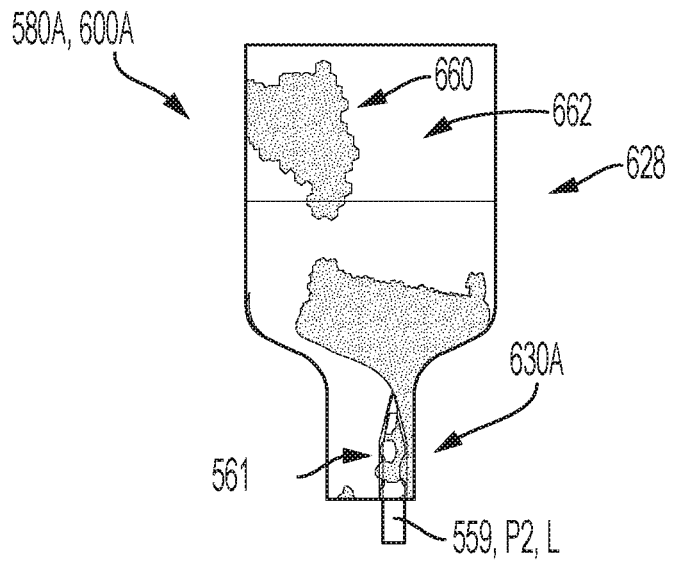
Figure 12F:
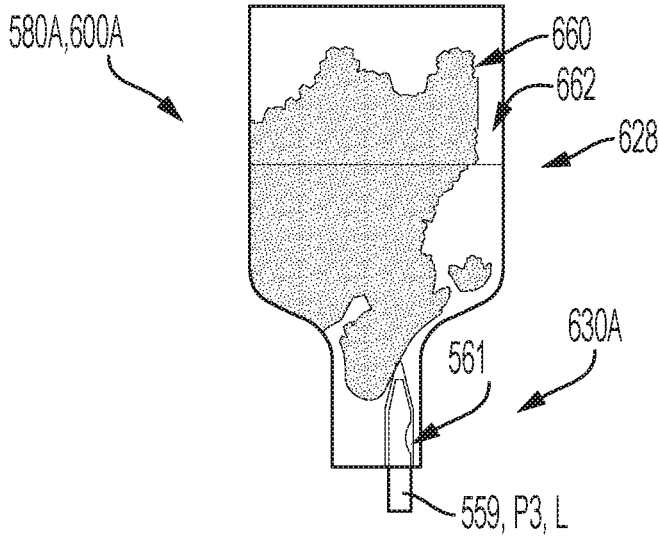
Figure 13A:
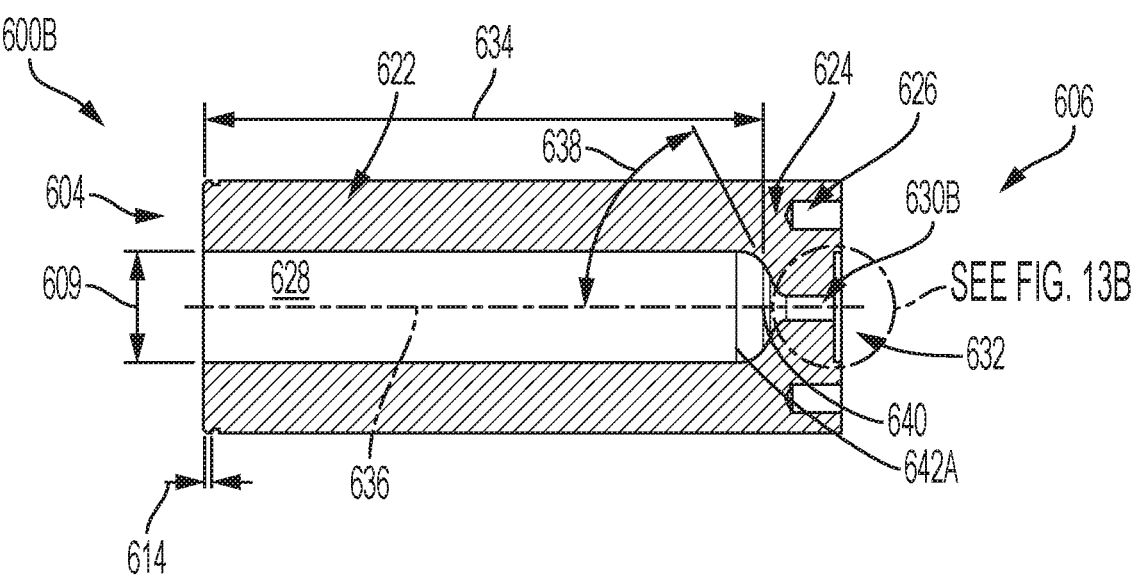
Figure 13B:
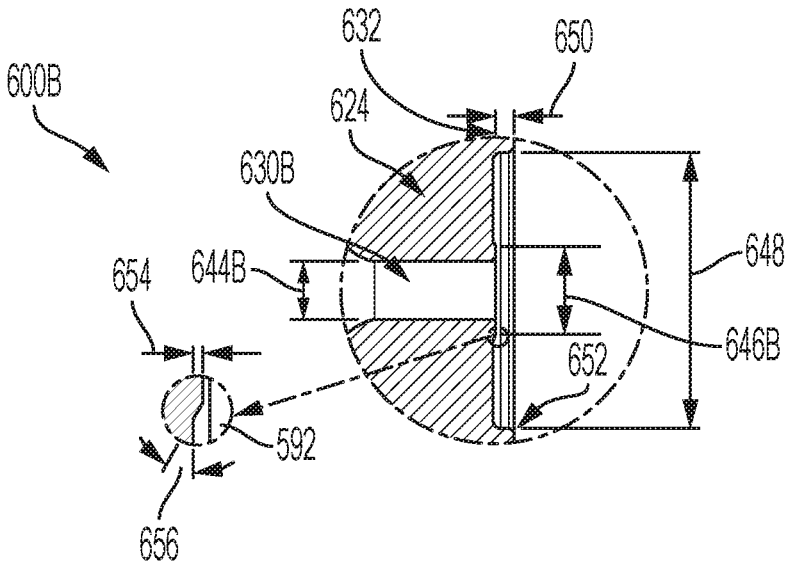
Figure 13C:
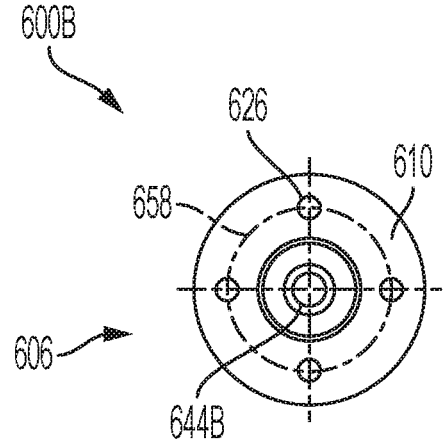
Figure 13D:
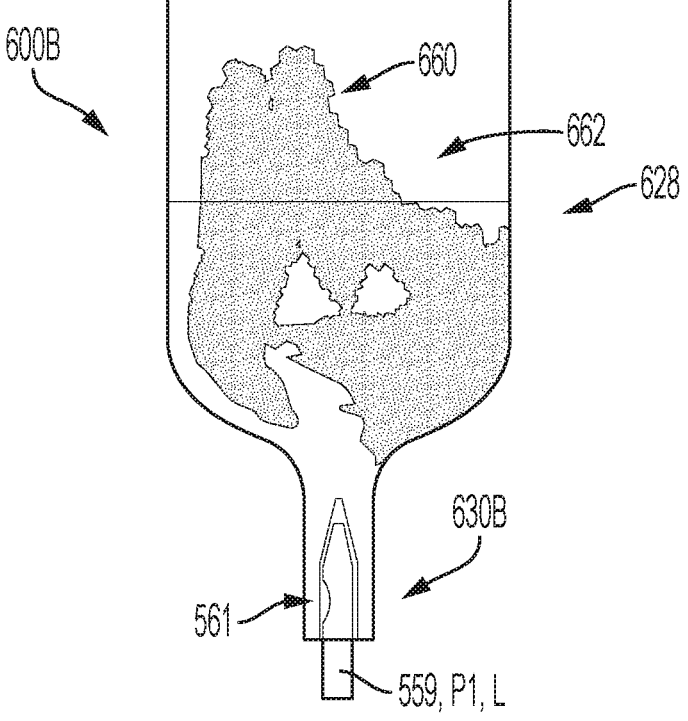
Figure 14A:
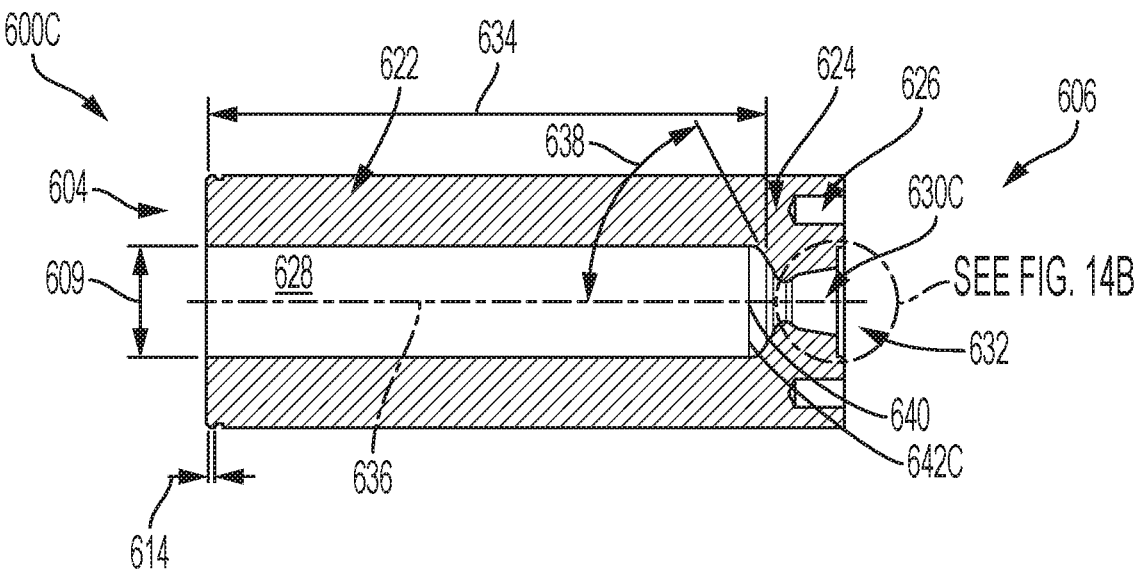
Figure 14B:
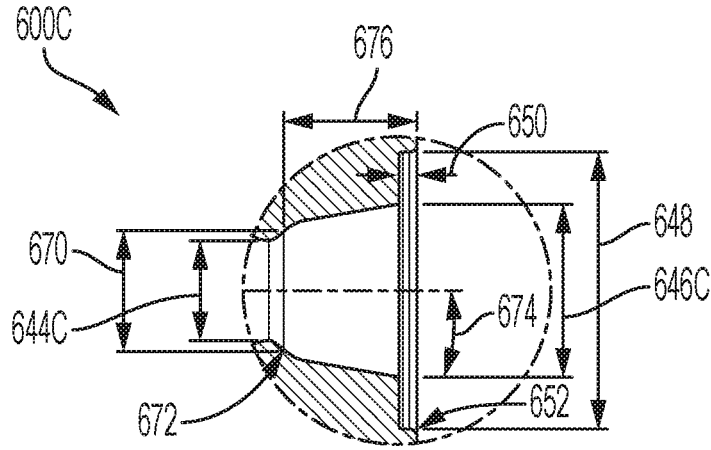
Figure 14C:
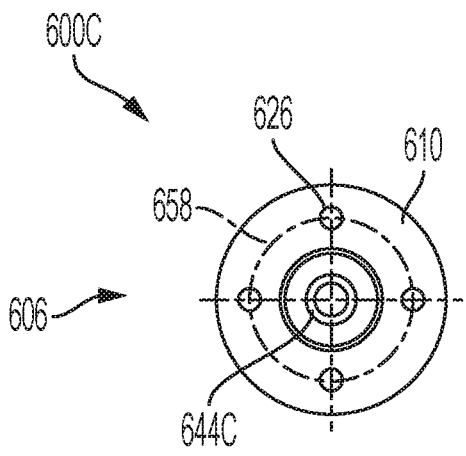
Figure 14D:
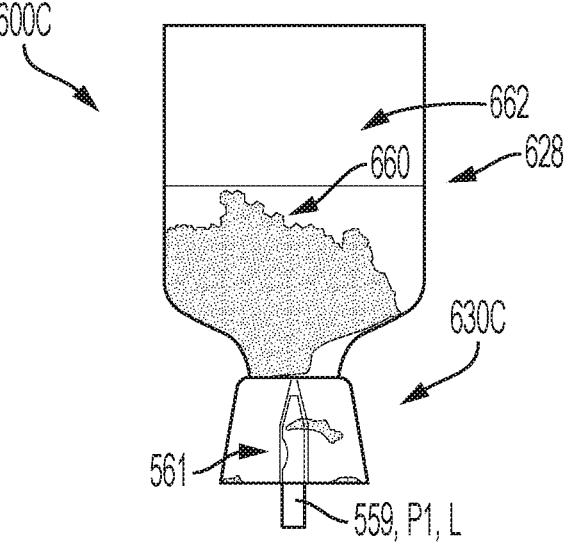
Figure 14E:
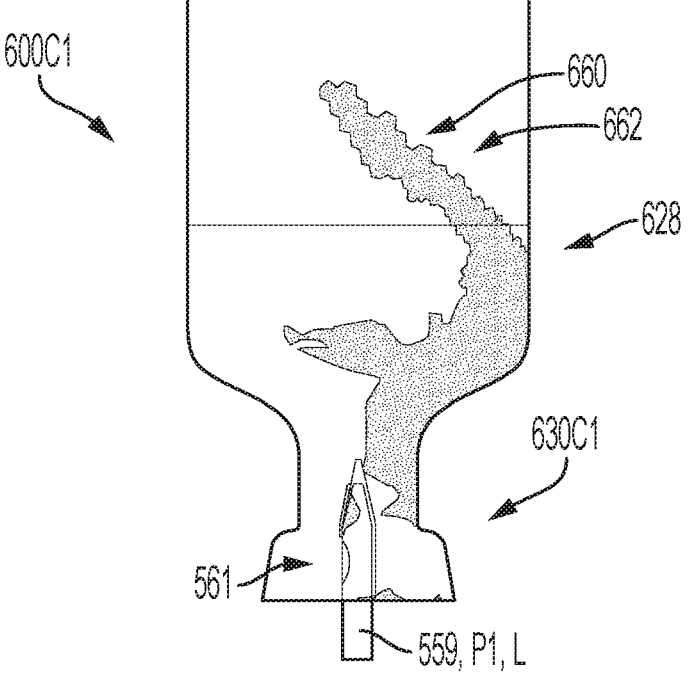
Figure 15A:
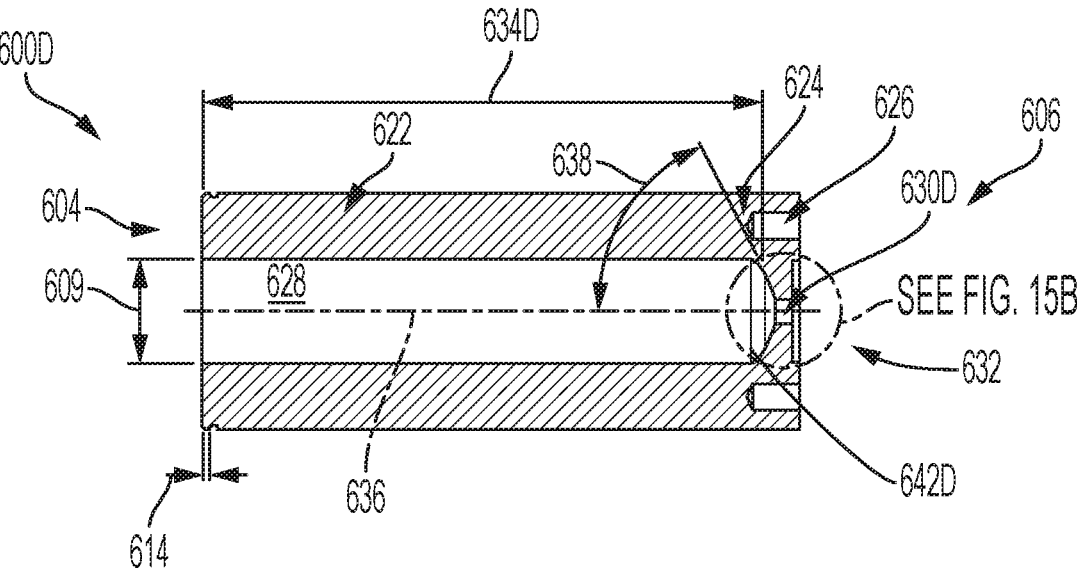
Figure 15B:
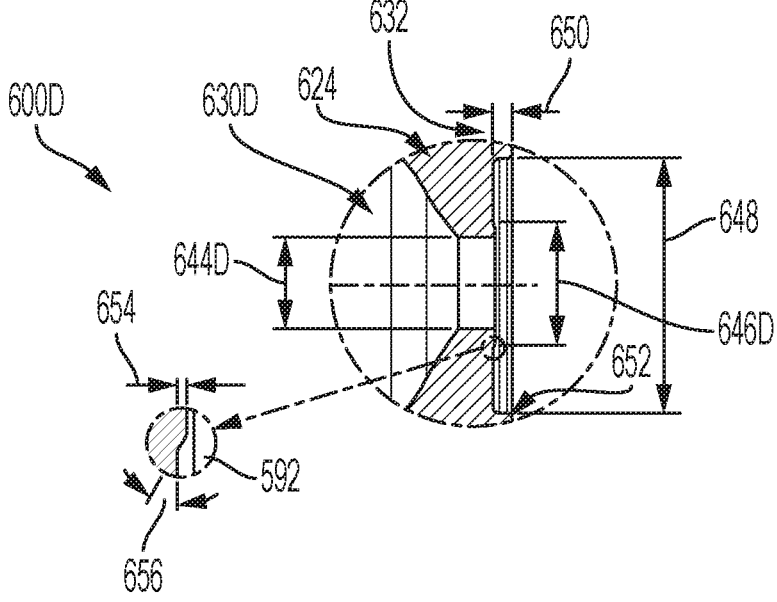
Figure 15C:
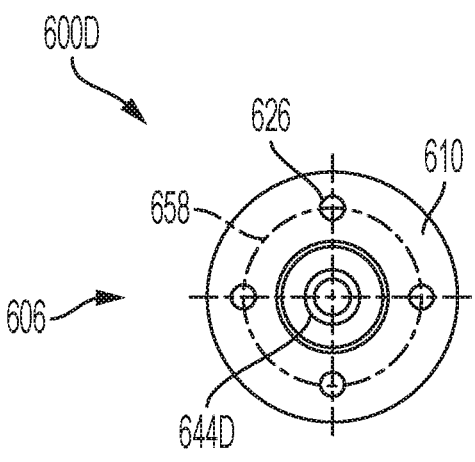
Figure 16:
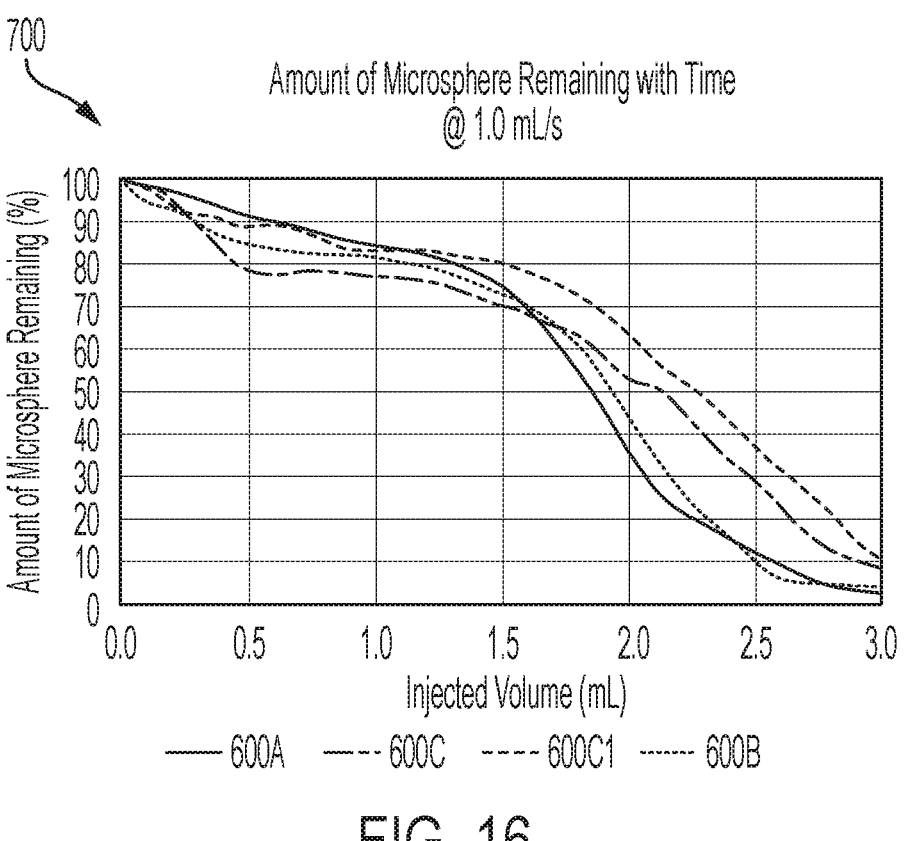
Figure 17:
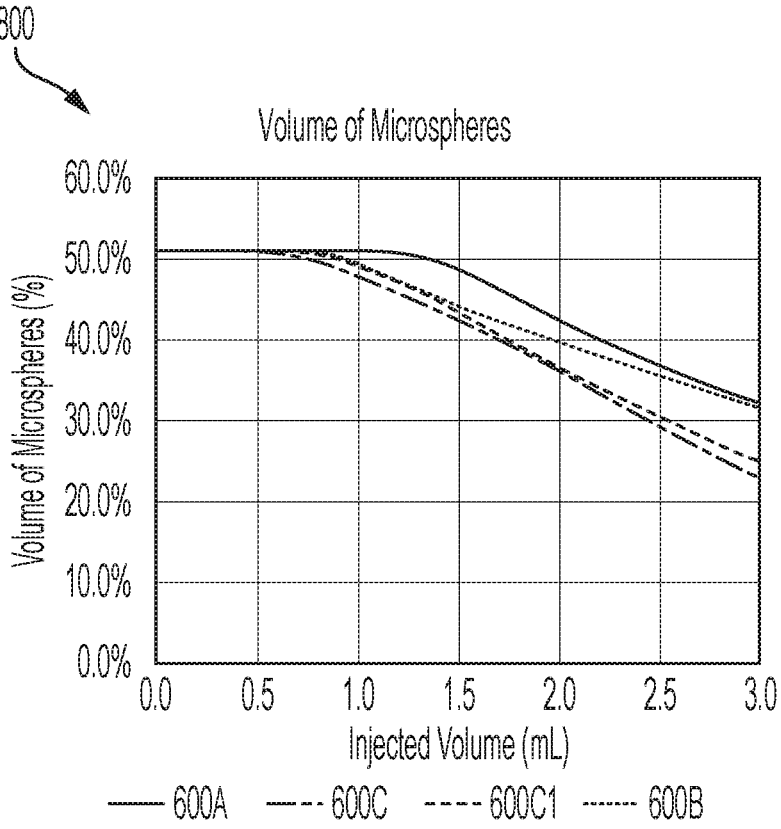

FIG. 11A is a perspective view of a vial according to one or more embodiments shown and described herein;

FIG. 11B is a side elevation view of the vial of FIG. 11A;

FIG. 11C is a detail view of a proximal edge of a proximal end of the vial of FIG. 11B;

FIG. 11D is a top distal view of the vial of FIG. 11A;

FIG. 12A is a cross-sectional view of an embodiment of the vial of FIG. 11A, with the cross-section taken along line 12A-12B of FIG. 11B;

FIG. 12B is a detail view of a neck region of the vial of FIG. 12A at a distal end;

FIG. 12C is a bottom proximal view of the vial of FIG. 12A;

FIG. 12D is an elevation view of a vial assembly including the vial of FIG. 12A, a needle disposed in the neck region of the vial, and a mixed fluid in the vial, with the needle in a first position, according to one or more embodiments shown and described herein;

FIG. 12E is the vial assembly of FIG. 12D with the needle in a second position;

FIG. 12F is the vial assembly of FIG. 12D with the needle in a third position;

FIG. 13A is a cross-sectional view of another embodiment of the vial of FIG. 11A, with the cross-section taken along line 12A-12B of FIG. 11B according to one or more embodiments shown and described herein;

FIG. 13B is a detail view of a neck region of the vial of FIG. 13A at a distal end;

FIG. 13C is a bottom proximal view of the vial of FIG. 13A;

FIG. 13D is an elevation view of a vial assembly including the vial of FIG. 13A, a needle disposed in the neck region of the vial, and a mixed fluid in the vial, with the needle in a first position, according to one or more embodiments shown and described herein;

FIG. 14A is a cross-sectional view of yet another embodiment of the vial of FIG. 11A, with the cross-section taken along line 12A-12B of FIG. 11B according to one or more embodiments shown and described herein;

FIG. 14B is a detail view of a neck region of the vial of FIG. 14A at a distal end;

FIG. 14C is a bottom proximal view of the vial of FIG. 14A;

FIG. 14D is an elevation view of a vial assembly including the vial of FIG. 14A, a needle disposed in the neck region of the vial, and a mixed fluid in the vial, with the needle in a first position, according to one or more embodiments shown and described herein;

FIG. 14E is an elevation view of a vial assembly including another conical embodiment of the vial of FIG. 14A, a needle disposed in the neck region of the vial, and a mixed fluid in the vial, with the needle in a first position, according to one or more embodiments shown and described herein;

FIG. 15A is a cross-sectional view of one other embodiment of the vial of FIG. 11A, with the cross-section taken along line 12A-12B of FIG. 11B according to one or more embodiments shown and described herein;

FIG. 15B is a detail view of a neck region of the vial of FIG. 15A at a distal end;

FIG. 15C is a bottom proximal view of the vial of FIG. 15A;

FIG. 16 is a graphical view of an amount of microspheres remaining for an injected volume over time for the vial assemblies of FIGS. 12D, 13D, 14D, and 14E according to one or more embodiments shown and described herein; and FIG. 17 is a graphical view of a volume of microspheres remaining for an injected volume over time for the vial assemblies of FIGS. 12D, 13D, 14D, and 14E according to one or more embodiments shown and described herein.

DETAILED DESCRIPTION

Reference will now be made in detail to various embodiments of delivery devices for administering radioactive compounds to a patient, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Unless otherwise defined, all technical and scientific terms used herein have the same meaning as commonly understood by one of ordinary skill in the art to which the disclosure belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal," "vertical," "distal" and "proximal" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present disclosure and the embodiments thereof to be described herein may be used in any desired orientation. Moreover, horizontal and vertical walls need generally only be intersecting walls, and need not be perpendicular. As used herein, the singular forms "a," "an" and "the" include plural referents unless the context clearly dictates otherwise. Thus, for example, reference to "a" component includes aspects having two or more such components, unless the context clearly indicates otherwise.

In embodiments described herein, a particulate material delivery assembly may include a radioembolization delivery device. A radioembolization delivery device comprises a medical device configured to deliver radioactive compounds to a treatment area within a patient's body in procedures such as transarterial radioembolization. The radioactive compounds may be a mixed solution of saline and radioactive microspheres (i.e., a particulate) mixed in a vial of a vial assembly. The needle may include one or more ports as an outlet to inject fluid (i.e., saline), such as from a syringe or catheter line, into a vial including the radioactive microspheres to generate the mixed solution and as an inlet to deliver the mixed solution to the patient.

FIGS. 1-10 described below are directed to an embodiment of a delivery device 500 to deliver a particulate 660, and FIGS. 11A-17 described in greater detail further below are directed to embodiments of one or more vials 600 that may be utilized as vials containing the particulate 660 and with, for example, the delivery device 600 to deliver the particulate 660. In some embodiments, as described in greater detail below, the delivery device 500 is a radioembolization delivery device, the particulate 660 is a plurality of radioembolization beads, the fluid is a saline solution, and the resulting mixed fluid (e.g., the mixed fluid solution) is a radioembolization beads-saline solution. The needle 559 may be configured to deliver the radioembolization beads-saline solution as the mixed fluid solution through the radioembolization delivery device, such as upon actuation of the vial engagement mechanism 520 in the positive pressure direction. In some embodiments, the fluid is a contrast-saline solution including a contrast agent, and the resulting mixed fluid (e.g., the mixed fluid solution) is a radioembolization beads-contrast-saline solution. The needle 559 may be configured to deliver the radioembolization beads-contrast-saline solution as the mixed fluid solution through the radioembolization delivery device. In some embodiments, the delivery device 500 is a chemoembolization delivery device, the particulate 660 is a plurality of chemoembolization beads, and the mixed fluid solution is a beads-saline solution or a beads-contrast-saline solution.

I. Mechanical Delivery Device with Removable Sled Assembly

FIGS. 1-10 show an embodiment of a delivery device 500 that is configured and operable to deliver a radioactive material (e.g., radioembolizing beads) while reducing radioactive emissions during use of the delivery device 500. The delivery device 500 may operate as described in International PCT App. No. PCT/2019/033001, filed May 17, 2019, the entirety of which is incorporated herein, except with respect to a vial 600 utilized with the delivery device 500 and as described in greater detail below with respect to FIGS. 11A-17 and in one or more embodiments herein.

Figure 1:
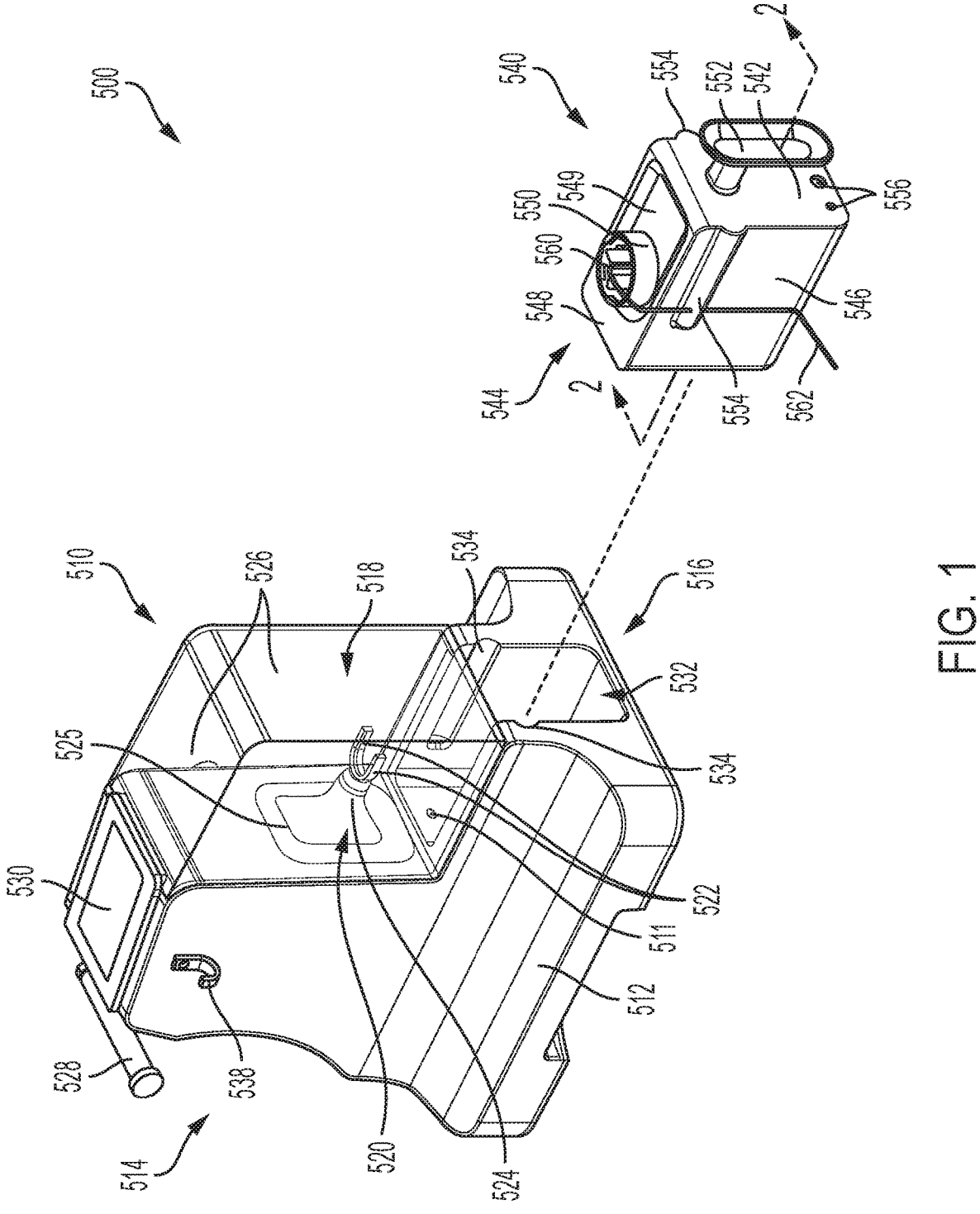
FIG. 1 is a perspective view of a delivery device including a protective shield and a vial sled according to one or more embodiments shown and described herein.

Referring initially to FIG. 1, the delivery device 500 comprises a console assembly 510, which includes a console. The delivery device 500 may include a sled assembly 540 that is operable to transition between a coupled state and decoupled state relative to the console assembly 510. The console assembly 510 of the delivery device 500 comprises a base 512 defined by and extending between a proximal end 514 and a distal end 516. The proximal end 514 of the base 512 includes a handle (delivery handle) 528 movably coupled to the console assembly 510 and an interface display 530 positioned on the console assembly 510.

The proximal end 514 of the base 512 further includes an attachment device 538 that is configured to securely retain an external device to the base 512 of the console assembly 510. The attachment device 538 is operable to facilitate an attachment of a complimentary device to the console assembly 510 for use with the delivery device 500 during a procedure.

Still referring to FIG. 1, the distal end 516 of the console assembly 510 defines a vial containment region 518 that is sized and shaped to receive the console assembly 510 therein, as will be described in greater detail herein. The console assembly 510 further includes a vial engagement mechanism 520 extending from the base 512 adjacent to the distal end 516. In particular, the vial engagement mechanism 520 extends laterally outward from the base 512 of the console assembly 510 toward the distal end 516. The vial engagement mechanism 520 is positioned within the vial containment region 518 of the console assembly 510 and is movably coupled to the handle 528. In particular, the handle 528 of the console assembly 510 is operable to move, and in particular translate, the vial engagement mechanism 520 within the vial containment region 518 in response to an actuation of the handle 528.

The console assembly 510 includes a mechanical assembly disposed within the base 512 that is configured and operable to convert a manual motion of the handle 528 to a corresponding linear displacement of the vial engagement mechanism 520. In the present example, the mechanical assembly is coupled to the handle 528 and the vial engagement mechanism 520 such that selective actuation of the handle 528 at the proximal end 514 causes a simultaneous actuation of the vial engagement mechanism 520 at the distal end 516.

The sled cavity 532 is sized and shaped to receive the sled assembly 540 therein. As will be described in greater detail herein, the sled assembly 540 is configured to store and administer therapeutic particles (e.g., radioactive beads, microspheres, medium) therethrough. In particular, the sled assembly 540 is configured to partially receive a vial assembly 580 therein for administering the therapeutic particles from the delivery device 500 and to a patient during a procedure.

Figure 2:
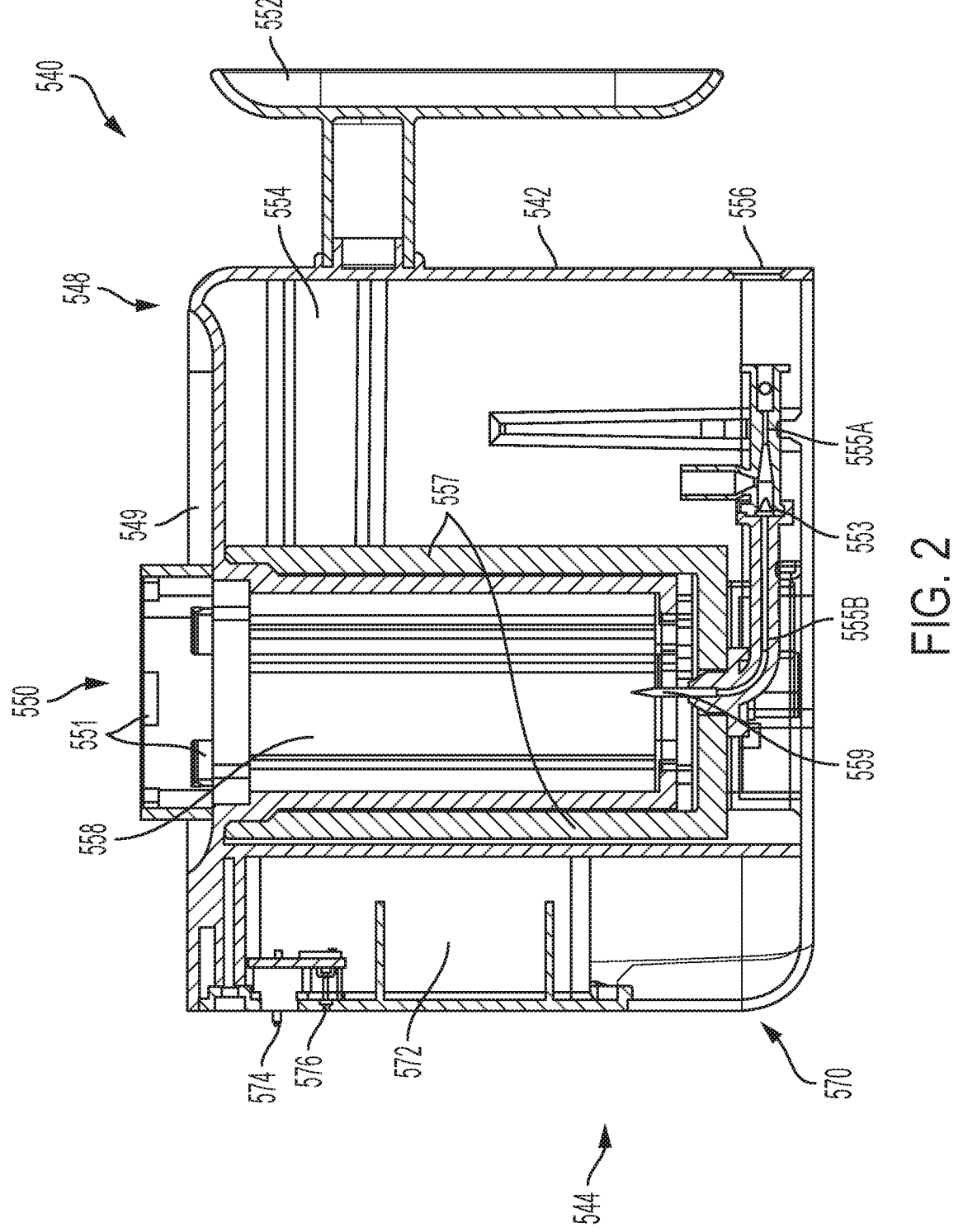
FIG. 2 is a cross-sectional view of the vial sled of FIG. 1 according to one or more embodiments shown and described herein, the cross-section along line 2-2 of FIG. 1.

In embodiments, and referring to FIG. 2, a flow sensor of the delivery device 500 may be positioned in-line with the tubing set of the delivery device 500, and in particular the needle 559, the manifolds 555A, 555B, and/or one or more of the ports 556, and may be configured to measure an amount of fluid (e.g., suspension liquid after the therapeutic particles have effectively mixed with the fluid medium) that passes thereby. Referring back to FIG. 1, the vial engagement mechanism 520 comprises a pair of lever arms 522 extending outwardly from a neck 524 of the vial engagement mechanism 520, with the neck 524 extending laterally outward from the base 512 of the console assembly 510. The neck 524 of the vial engagement mechanism 520 is disposed within a protective cover 525 such that only the pair of lever arms 522 of the vial engagement mechanism 520 extends through the protective cover 525. The protective cover 525 is operable to shield one or more internal components of the console assembly 510 from an exterior of the console assembly 510, and in particular from the vial containment region 518.

The pair of lever arms 522 is simultaneously movable with the neck 524 of the vial engagement mechanism 520 in response to an actuation of the handle 528 of the console assembly 510. Further, the pair of lever arms 522 are fixed relative to one another such that a spacing formed between the pair of lever arms 522 is relatively fixed. The pair of lever arms 522 of the vial engagement mechanism 520 is configured to securely engage the vial assembly 580 therebetween, and in particular within the spacing formed by the pair of lever arms 522. Accordingly, the vial engagement mechanism 520 is operable to securely attach the vial assembly 580 to the console assembly 510 at the vial containment region 518. Although the vial engagement mechanism 520 is shown and described herein as including a pair of lever arms 522, it should be understood that the vial engagement mechanism 520 may include various other structural configurations suitable for engaging the vial assembly 580.

Still referring to FIG. 1, the console assembly 510 further includes a safety shield 526 secured to the distal end 516 of the base 512 along the vial containment region 518. In particular, the safety shield 526 is a protective covering that is sized and shaped to enclose the vial containment region 518 of the console assembly 510 when secured thereon. The safety shield 526 is selectively attachable to the distal end 516 of the base 512 and is formed of a material that is configured to inhibit radioactive emissions from one or more radioactive doses stored within the vial containment region 518.

The distal end 516 of the console assembly 510 further includes a sled cavity 532 that is sized and shaped to receive the sled assembly 540 therein. The sled cavity 532 includes a pair of alignment features 534 extending therein, with the alignment features 534 sized and shaped to correspond with complimentary alignment features of the sled assembly 540 (e.g., alignment ribs 554) to thereby facilitate a coupling of the sled assembly 540 with the base 512 of the console assembly 510 within the sled cavity 532.

Still referring to FIG. 1, the sled assembly 540 is configured to partially receive a vial assembly 580 therein for administering therapeutic particles (e.g., radioactive fluid medium) from the delivery device 500 and to a patient. In particular, the sled assembly 540 comprises a proximal end 542 and a distal end 544 with a pair of sidewalls 546 extending therebetween. The proximal end 542 of the sled assembly 540 includes a handle 552 extending proximally therefrom. The handle 552 is configured to facilitate movement of the sled assembly 540, and in particular, an insertion of the sled assembly 540 into the sled cavity 532 of the console assembly 510. The proximal end 542 further includes one or more ports 556 for coupling one or more delivery lines (i.e., tubing) to the sled assembly 540. With the one or more delivery lines further be coupled to one or more external devices at an end of the line opposite of the ports 556, the ports 556 effectively serve to fluidly couple the sled assembly 540 to the one or more external devices via the delivery lines connected thereto. The pair of sidewalls 546 of the sled assembly 540 includes at least one alignment rib 554 extending laterally outward therefrom, where the alignment ribs 554 are sized and shaped to correspond with and mate to the pair of alignment features 534 of the console assembly 510. Accordingly, the pair of alignment ribs 554 are configured to facilitate an alignment and engagement of the sled assembly 540 with the console assembly 510 when the distal end 544 is slidably received within the sled cavity 532 of the base 512.

The sled assembly 540 further includes a top surface 548 extending from the proximal end 542 and the distal end 544 and positioned between the pair of sidewalls 546. The top surface 548 of the sled assembly includes a recessed region

549 and a locking system 550. The recessed region 549 is sized and shaped to form a recess and/or cavity along the top surface 548, where the recessed region 549 is capable of receiving and/or collecting various materials therein, including, for example, leaks of various fluid media during use of the delivery device 500. The locking system 550 of the sled assembly 540 forms an opening along the top surface 548 that is sized and shaped to receive one or more devices therein, such as a priming assembly 560 and a vial assembly 580. In some embodiments, the sled assembly 540 comes preloaded with the priming assembly 560 disposed within the locking system 550. The priming assembly 560 includes a priming line 562 extending outwardly from the locking system 550 of the sled assembly 540. The priming assembly 560 serves to purge the delivery device 500 of air prior to utilizing the delivery device 500 in a procedure.

Referring now to FIG. 2, the locking system 550 includes an annular array of projections 551 extending outwardly therefrom, and in particular, extending laterally into the aperture formed by the locking system 550 along the top surface 548. The annular array of projections 551 are formed within an inner perimeter of the locking system 550 and extend along at least two sequentially-arranged rows. The annular array of projections 551 included in the locking system 550 are configured to engage a corresponding locking feature 586 of the vial assembly 580 (See FIG. 3) to thereby securely fasten the vial assembly 580 to the sled assembly 540. It should be understood that the multiple rows of projections 551 of the locking system 550 serve to provide a double-locking system to ensure the sled assembly 540, and in particular a needle 559 of the sled assembly 540, is securely maintained through a septum 592 of the vial assembly 580 (See FIG. 3) during use of the delivery device 500 in a procedure.

The sled assembly 540 further includes a vial chamber 558 that is sized and shaped to receive the priming assembly 560 and the vial assembly 580 therein, respectively. In other words, the vial chamber 558 is sized to individually receive both the priming assembly 560 and the vial assembly 580 separate from one another. The vial chamber 558 is encapsulated around a protective chamber or shield 557 disposed about the vial chamber 558. The protective shield 557 is formed of a material configured to inhibit radioactive emissions from extending outwardly from the vial chamber 558, such as, for example, a metal. Additionally, the sled assembly 540 includes a needle extending through the protective shield 557 and into the vial chamber 558 along a bottom end of the vial chamber 558. The needle 559 is fixedly secured relative to the vial chamber 558 such that any devices received through the aperture of the locking system 550 and into the vial chamber 558 are to encounter and interact with the needle 559 (e.g., the priming assembly 560, the vial assembly 580, and the like).

Still referring to FIG. 2, the needle 559 is coupled to a distal manifold 555A and a proximal manifold 555B disposed within the sled assembly 540, and in particular the manifold 555A, 555B is positioned beneath the vial chamber 558 and the protective shield 557. The proximal manifold 555B is fluidly coupled to the needle 559 and the distal manifold 555A is fluidly coupled to the one or more ports 556 of the sled assembly 540. The proximal manifold 555B is in fluid communication with the distal manifold 555A through a one-way check valve 553 disposed therebetween.

Accordingly, the proximal manifold 555B is in fluid communication with the one or more ports 556 via the distal manifold 555A, however, the one or more ports 556 are not in fluid communication with the proximal manifold 555B due to a position of the one-way check valve 553 disposed between the manifolds 555A, 555B. Thus, the needle 559 is in fluid communication with the one or more delivery lines and/or devices coupled to the sled assembly 540 at the one or more ports 556 via the manifolds 555A, 555B secured therebetween. The one or more ports 556 of the sled assembly 540 may be coupled to a bag (e.g., saline bag), a syringe, a catheter, and/or the like via one or more delivery lines coupled thereto. In other embodiments, the needle 559 may be a cannula, catheter, or similar mechanism through which to inject and receive fluid and/or a solution as described herein.

Still referring to FIG. 2, the sled assembly 540 includes a removable battery pack 570 coupled to the sled assembly 540 along the distal end 544. The removable battery pack 570 comprises a battery 572, electrical contacts 574, and a removable tab 576. The battery 572 of the delivery device 500 is isolated from one or more fluid paths and radiation sources due to a location of the battery 572 in the removable battery pack 570.

The electrical contacts 574 of the removable battery pack 570 extend outwardly from the removable battery pack 570 and are operable to contact against and interact with corresponding electrical contacts 511 of the console assembly 510 (See FIG. 1) when the sled assembly 540 is coupled to the base 512 at the sled cavity 532. Accordingly, the removable battery pack 570 is operable to provide electrical power to the delivery device 500, and in particular the console assembly 510, when the sled assembly 540 is coupled to the console assembly 510.

Additionally, as will be described in greater detail herein, in some embodiments the locking system 550 may include at least one planar wall relative to a remaining circular orientation of the locking system 550. In this instance, an aperture formed by the locking system 550 through the top surface 548 of the sled assembly 540 is irregularly-shaped, rather than circularly-shaped as shown and described above. In this instance, the vial assembly 580 includes an locking feature 586 that has a shape and size that corresponds to the locking system 550, and in particular the at least one planar wall such that the vial assembly 580 is received within the sled assembly 540 only when an orientation of the vial assembly 580 corresponds with an alignment of the locking feature 586 and the locking system 550. In other words, a corresponding planar wall 586A of the locking feature 586 (See FIG. 3) must be aligned with the planar wall of the locking system 550 for the vial assembly 580 to be receivable within an aperture formed by the locking system 550 of the sled assembly 540.

Figure 3:
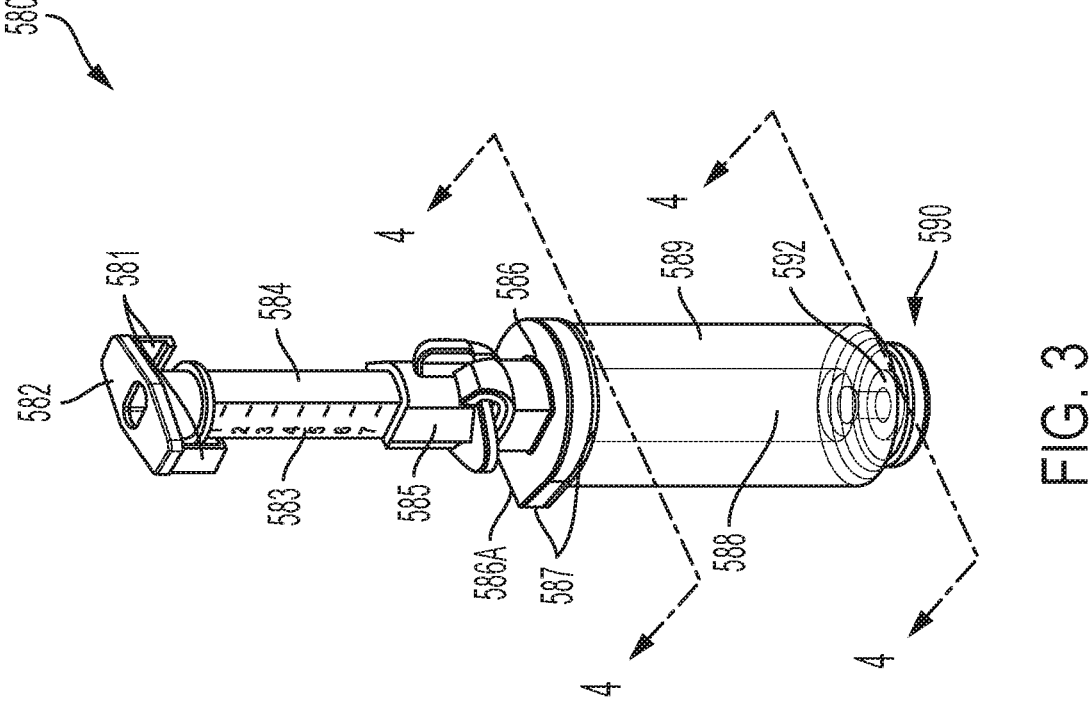
FIG. 3 is a perspective view of a vial assembly including an engagement head according to one or more embodiments shown and described herein.

Referring now to FIG. 3, the vial assembly 580 of the delivery device 500 is depicted. The vial assembly 580 comprises an engagement head 582, a plunger 584, an locking feature 586, and a vial body 589. In particular, the engagement head 582 of the vial assembly 580 is positioned at a terminal end of the plunger 584 opposite of the locking feature 586 and the vial body 589. The engagement head 582 includes a pair of arms 581 extending laterally outward relative to a longitudinal length of the plunger 584 extending downwardly therefrom. In the present example, the engagement head 582 is integrally formed with the plunger 584, however, it should be understood that in other embodiments the engagement head 582 and the plunger 584 may be separate features fastened thereto. In either instance, the engagement head 582 and the plunger 584 is movable relative to the locking feature 586 and the vial body 589 such that the engagement head 582 and the plunger 584 are slidably translatable through the locking feature 586 and the vial body 589. In particular, as will be described in greater detail herein, the plunger 584 may translate into and out of an internal chamber 588 of the vial body 589 in response to a linear translation of the vial engagement mechanism 520 when the engagement head 582 is secured to the pair of lever arms 522.

The plunger 584 includes a plurality of indicia and/or markings 583 positioned along a longitudinal length of the plunger 584. The plurality of markings 583 is indicative of a relative extension of the engagement head 582 and the plunger 584 from the locking feature 586 and the vial body 589. As briefly noted above, the engagement head 582 is configured to attach the vial assembly 580 to the vial engagement mechanism 520. In particular, the pair of arms 581 of the engagement head 582 are sized and shaped to couple with the pair of lever arms 522 of the vial engagement mechanism 520 when the vial assembly 580 is received within the sled assembly 540 and the sled assembly is inserted into the sled cavity 532 of the console assembly 510. As will be described in greater detail herein, the pair of lever arms 522 are received between the pair of arms 581 of the engagement head 582 and the plunger 584 in response to a predetermined translation force applied to the vial engagement mechanism 520. The engagement head 582 and the plunger 584 may be formed of various materials, including, but not limited to, a metal, plastic, and/or the like.

Still referring to FIG. 3, the vial assembly 580 further includes a safety tab 585 coupled to the plunger 584 relatively above the locking feature 586 and below the engagement head 582 such that the safety tab 585 is positioned along the longitudinal length of the plunger 584. The safety tab 585 may be formed of various materials, such as, for example, a plastic, and is preassembled onto the vial assembly 580 prior to a use of the delivery device 500. The safety tab 585 is removably fastened to the plunger 584 and inhibits the plunger 584 from translating relative to the vial body 589. In particular, the safety tab 585 abuts against the locking feature 586 in response to an application of linear force onto the plunger 584 to translate the plunger 584 relatively downward into the vial body 589. In this instance, the safety tab 585 is configured to inhibit an inadvertent movement of the plunger 584, and in response, an inadvertent delivery of a fluid media stored within the internal chamber 588 of the vial body 589 (e.g., therapeutic particles, radioembolizing beads). As will be described in greater detail herein, the safety tab 585 is selectively disengaged from the plunger 584 in response to a coupling of the vial assembly 580 with the vial engagement mechanism 520, and in particular an engagement of the pair of lever arms 522 with the engagement head 582.

Referring back to FIG. 3, the locking feature 586 extends about a top end of the vial body 589. In the present example, the locking feature 586 of the vial assembly 580 comprises a bushing that defines a lateral edge 587 extending laterally outward along an outer perimeter of the locking feature 586. The lateral edge 587 of the locking feature 586 is sized and shaped to engage the annular array of projections 551 of the locking system 550 when the vial assembly 580 is received within the vial chamber 558 of the sled assembly 540. As will be described in greater detail herein, the locking feature 586, and in particular the lateral edge 587 of the locking feature 586, is configured to securely fasten the vial assembly 580 to the locking system 550 to inhibit removal of the vial body 589 from the vial chamber 558 of the sled assembly 540 during use of the delivery device 500 in a procedure. In some embodiments, as briefly described above, the locking feature 586 includes at least one planar wall 586A such that the locking feature 586 comprises an irregular-profile. The at least one planar wall 586A is configured to correspond to the planar wall 550A of the locking system 550 such that an alignment of the planar walls 550A, 586A is required for the vial assembly 580 to be received through an aperture formed by the locking system 550.

Still referring to FIG. 3, the vial body 589 extends downwardly relative from the locking feature 586 and has a longitudinal length that is sized to receive at least a portion of a longitudinal length of the plunger 584 therein. By way of example only, a longitudinal length of the vial body 589 may be about 8 millimeters to about 10 millimeters, and in the present example comprises 9 millimeters, while a longitudinal length of the plunger 584 may be about 9 millimeters to about 11 millimeters, and in the present example comprises 10 millimeters. Accordingly, in some embodiments a longitudinal length of the plunger 584 exceed a longitudinal length of the vial body 589 such that a translation of the plunger 584 into the internal chamber 588 of the vial body 589 causes a fluid media stored therein to be transferred outward from the vial body 589. As will be described in greater detail herein, a translation of the plunger 584 through the internal chamber 588 of the vial body 589 provides for an administration of a fluid media stored within the vial body 589 outward from the vial assembly 580. The vial body 589 may be formed of various materials, including, for example, a thermoplastic polymer, copolyester, polycarbonate, a biocompatible plastic, polysulfone, ceramics, metals, and/or the like.

The vial body 589 is of the present example is formed of a material that is configured to inhibit radioactive emissions from a fluid media stored within the internal chamber 588 of the vial body 589. For example, the vial body 589 may be formed of a plastic, such as polycarbonate, and have a width of approximately 9 millimeters (mm). A density and material composition of the vial body 589 may collectively inhibit beta radiation emission from electron particles stored within the internal chamber 588. In the present example, a chemical composition of the plastic of the vial body 589, along with the 9 mm wall thickness, provides a plurality of atoms disposed within the vial body 589 that are capable of encountering the electron particles generating beta radiation and reducing an emission of said radiation from the vial assembly 580. Accordingly, the vial assembly 580 allows an operator to handle the radioactive material stored within the vial body 589 without being exposed to beta radiation. It should be understood that various other materials and/or wall sections may be incorporated in the vial body 589 of the vial assembly 580 in other embodiments without departing from the scope of the present disclosure.

Still referring to FIG. 3, the vial body 589 of the vial assembly 580 is sealed at a first terminal end 598 by the locking feature 586. The vial assembly 580 further includes a cap 590 positioned at an opposing, terminal end of the vial body 589 opposite of the locking feature 586, such that the cap 590 seals a second terminal end of the vial body 589 of the vial assembly 580. Additionally, the vial assembly 580 includes a septum 592 positioned adjacent to the cap 590 and in fluid communication with a terminal end of the vial body 589 opposite of the locking feature 586. The septum 592 forms a seal against a terminal end of the vial body 589 and the cap 590 retains the septum 592 therein. The septum 592 may be formed of various materials, including, for example, an elastomer, silicon, bromobutyl elastomer, rubber, urethanes, and/or the like. The septum 592 is configured to provide an air-tight seal for the vial body 589 to thereby inhibit a release of a fluid media stored therein (e.g., radioembolizing beads). As will be described in greater detail herein, the septum 592 of the vial assembly 580 is configured to be punctured by the needle 559 of the sled assembly 540 when the vial assembly 580 is received within the vial chamber 558, thereby establishing fluid communication between the vial body 589 and the sled assembly 540. In other embodiments, the septum 592 may be omitted entirely for an alternative device, such as, for example, a valve system, needle injection port, and/or the like.

Figure 4:
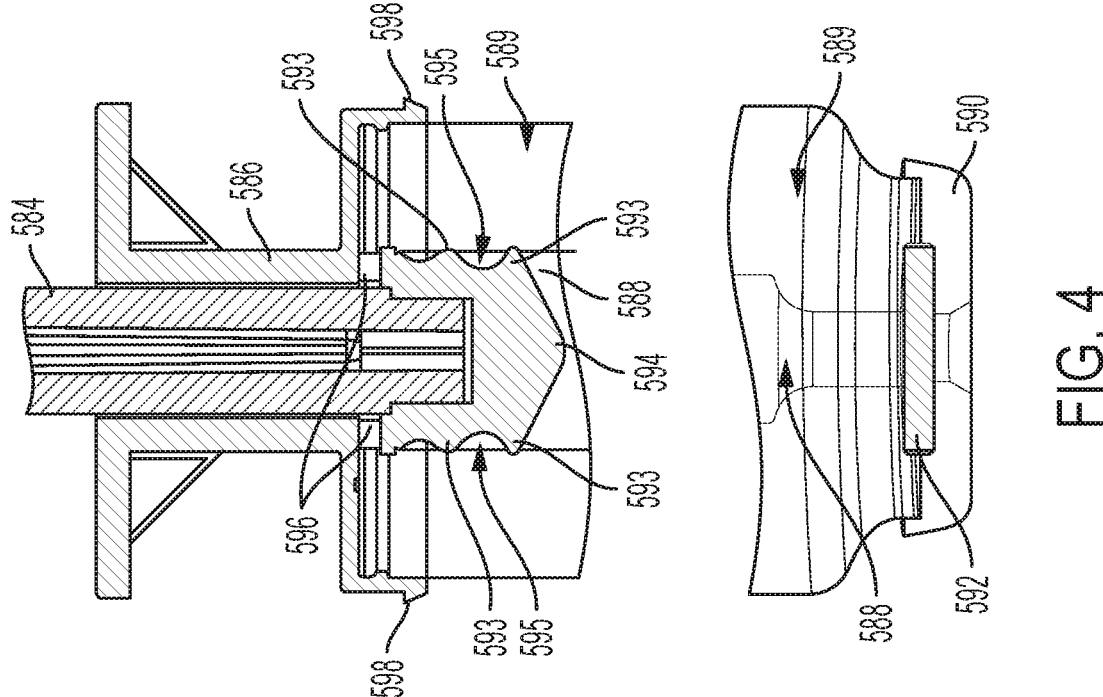
FIG. 4 is a partial cross-sectional view of the vial assembly of FIG. 4, the cross-section taken along line 4-4 of FIG. 3.
Figure 4:
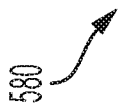

Referring to FIG. 4, the vial assembly 580 further includes a stopper 594 fixedly coupled to a terminal end of the plunger 584 opposite of the engagement head 582. In this instance, with the plunger 584 coupled to, and slidably translatable through, the internal chamber 588 of the vial body 589, the stopper 594 is effectively disposed within the vial body 589. Accordingly, it should be understood that the stopper 594 is sized and shaped in accordance with a size (e.g., a diameter) of the internal chamber 588 of the vial body 589. The stopper 594 is secured to the plunger 584 such that the stopper 594 is slidably translatable through the vial body 589 in response to a translation of the plunger 584 through the vial body 589. The stopper 594 is defined by two or more ribs 593 extending laterally outward and one or more troughs 595 defined between at least two ribs 593.

The stopper 594 is configured to form a liquid-seal against the internal chamber 588 of the vial body 589, and is formed of a various polymers with a predetermined viscoelasticity. For example, in some embodiments the stopper 594 is formed of an elastomer, silicone, rubber, urethane, plastic, polyethylene, polypropylene, and/or the like. In this instance, the stopper 594 is operable to inhibit a fluid media stored within the vial body 589 from extending (i.e., leaking) past the stopper 594 and out of the vial body 589. In particular, the two or more ribs 593 of the stopper 594 abut against, and form a seal along, the internal chamber 588 of the vial body 589 to thereby inhibit a fluid media from passing beyond the ribs 593. The one or more troughs 595 formed between the two or more ribs 593 of the stopper 594 are configured to receive, and more specifically capture, any fluid media that may inadvertently extend (i.e., leak) beyond the ribs 593 of the stopper 594. Accordingly, the one or more troughs 595 serve as a safety mechanism of the vial assembly 580 to ensure a fluid media is maintained within the vial body 589 and not exposed beyond the vial assembly 580.

Still referring to FIG. 4, the two or more ribs 593 of the stopper 594 are additionally configured to push a fluid media stored within the vial body 589 in one or more directions therein (e.g., toward the cap 590) in response to a translation of the plunger 584. With the ribs 593 of the stopper 594 pressed against the internal chamber 588 of the vial body 589, translation of the plunger 584 provides for a translation of the ribs 593 against and along the internal chamber 588 of the vial body 589 such that any fluid media located in front (i.e., beneath) of the stopper 594 is effectively redirected within the vial body 589 in a direction of travel of the plunger 584 and the stopper 594. The vial assembly 580 further includes an annular washer 596 disposed within the vial body 589. In particular, the annular washer 596 is securely fixed to the plunger 584 adjacent to the stopper 594, which is secured to the plunger 584 at a terminal end opposite of the engagement head 582. Accordingly, the annular washer 596 is secured to the plunger 584 and disposed within the vial body 589 adjacent to the stopper 594. With the annular washer 596 secured to the plunger 584 adjacent to the stopper 594, the annular washer 596 is effectively disposed within the vial body 589.

Figure 5:
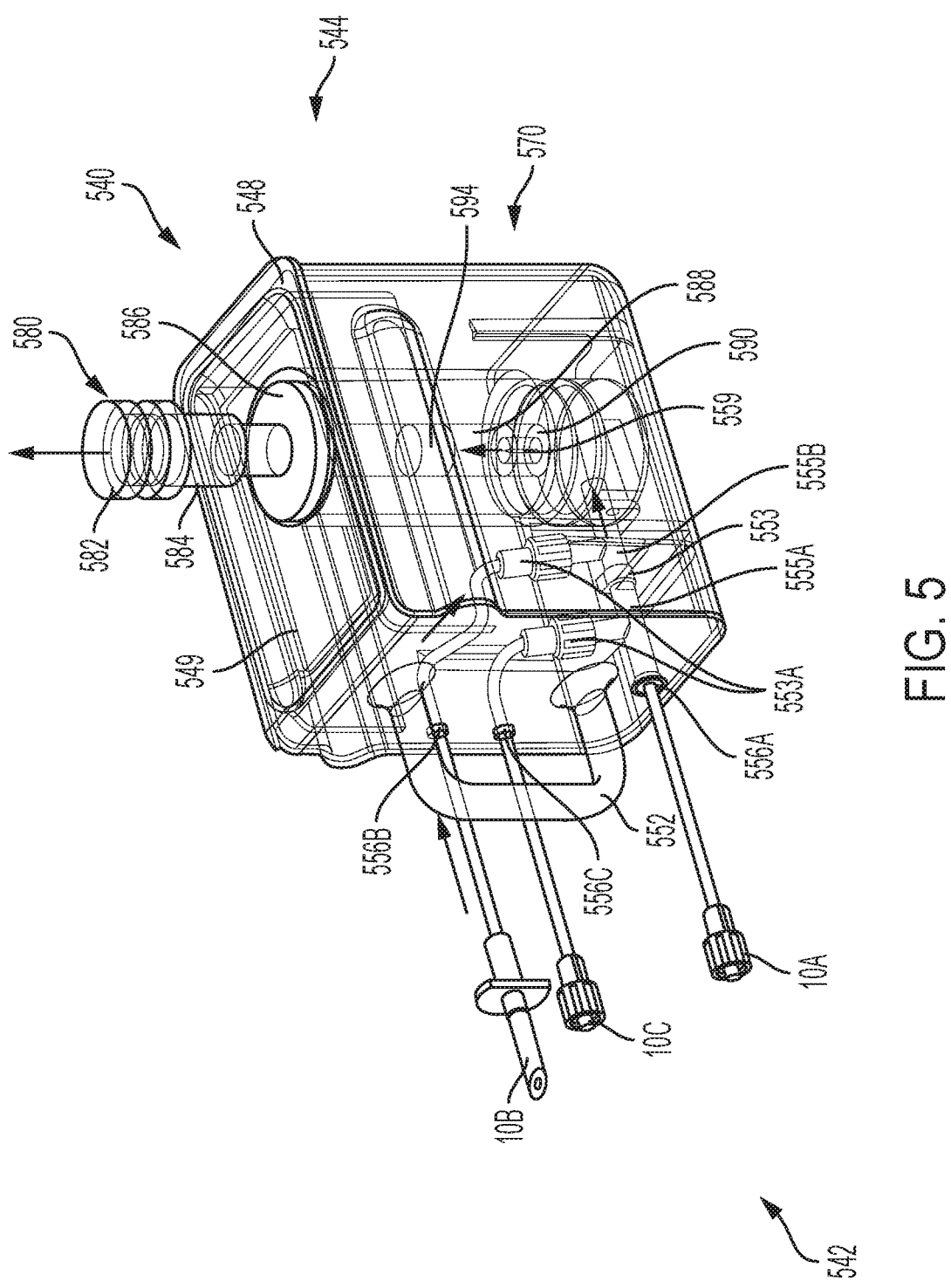
FIG. 5 is a perspective view of the vial sled of FIG. 1 with the vial assembly of FIG. 3 received therein, with a series of delivery lines coupled to the vial sled according to one or more embodiments shown and described herein.

Referring now to FIG. 5, in response to determining that the battery 572 contains or other power source provides a sufficient amount of power, one or more delivery lines are coupled to the sled assembly 540 via the one or more ports 556. In particular, a dose delivery line 10A is coupled to the sled assembly 540 at a delivery port 556A, a contrast line 10B is coupled to the sled assembly 540 at a contrast port 556B, and a flushing line 10C is coupled to the sled assembly 540 at a flushing port 556C. An opposing end of the dose delivery line 10A is initially coupled to a fluid reservoir, such as, for example, a collection bowl. As will be described in greater detail herein, the dose delivery line 10A may be subsequently coupled to an external device, such as a catheter, once the sled assembly 540 has been effectively primed by a fluid medium via the contrast line 10B. An opposing end of the flushing line 10C is coupled to an external device, such as, for example, a syringe. With both the dose delivery line 10A and the flushing line 10C coupled to the sled assembly 540, the sled assembly 540 is flushed with a fluid medium (e.g., saline) from the syringe coupled to the flushing line 10C. In this instance, the fluid medium is injected through the flushing line 10C, into the distal manifold 555A of the sled assembly 540, and out of the sled assembly 540 through the dose delivery line 10A. Accordingly, the fluid medium is ultimately received at the collection bowl and disposed thereat by the dose delivery line 10A.

With the distal manifold 555A of the sled assembly 540 separated from the proximal manifold 555B by the one-way valve 553 disposed therebetween, the fluid medium flushed through the distal manifold 555A from the syringe (via the flushing port 556C) is prevented from passing through the proximal manifold 555B and the needle 559 coupled thereto. Rather, the fluid medium injected from the syringe and through the flushing line 10C is received at the flushing port 556C, passed through the distal manifold 555A in fluid communication with the flushing port 556C, and redirected by the one-way valve 553 towards the dose delivery port 556A that is coupled to the dose delivery line 10A. In this instance, the dose delivery line 10A receives and transfers the fluid medium to the collection bowl coupled thereto, such that the fluid medium is not directed beyond the one-way valve 553 and into the proximal manifold 555B that is in fluid communication with the needle 559.

The contrast line 10B is coupled to the sled assembly 540 at a contrast port 556B. An opposing end of the contrast line 10B is coupled to a fluid medium supply, such as, for example, a bag secured to the console assembly 510 via the attachment device 538. In the present example, the bag is a saline bag such that the fluid medium stored therein is saline. In this instance, with the sled assembly 540 including the priming assembly 560 positioned within the vial chamber 558 and the needle end 568 in fluid communication with the needle 559, a syringe is fluidly coupled to the priming line 562 of the priming assembly 560 and a plunger of the syringe is drawn back to pull saline through the contrast line 10B, the contrast port 556B, the sled assembly 540, the priming line 562 and into the syringe from the saline bag. The plunger of the syringe is thereafter pushed inwards to transfer the extracted saline back through the priming line 562, the central body 564, the elongated shaft 566, and the needle end of the priming assembly 560 such that the saline is received into the needle 559 of the sled assembly 540. Accordingly, the manifolds 555A, 555B of the sled assembly 540 are effectively primed with the saline from the syringe as the needle 559 that received the saline from the priming assembly 560 is in fluid communication with the manifolds 555A, 555B. With the manifolds 555A, 555B in further fluid communication with the dose delivery line 10A via the delivery port 556A, the saline is effectively distributed to the collection bowl coupled thereto.

Referring now to FIG. 5, the sled assembly 540 is coupled to one or more external devices via the one or more ports 556. In particular, the sled assembly 540 is fluidly coupled to a catheter (e.g., microcatheter) via the dose delivery line 10A that is coupled to the delivery port 556A of the sled assembly 540. In this instance, the catheter is in fluid communication with the sled assembly 540 via the dose delivery line 10A. Further at step 718, the sled assembly 540 is fluidly coupled to a contrast source, such as, for example, a saline bag secured to the console assembly 510 via the attachment device 538 (See FIG. 1). The sled assembly 540 is in fluid communication with the saline bag via a contrast line 10B coupled to the contrast port 556B of the sled assembly 540. In this instance, the saline bag is in fluid communication with the sled assembly 540 via the contrast line 10B secured to the contrast port 556B.

The contrast port 556B is in fluid communication with the proximal manifold 555B while the delivery port 556A is in fluid communication with the distal manifold 555A. As will be described in greater detail herein, saline from the saline bag may be withdrawn through the needle 559 of the sled assembly 540 and into the vial body 589 of the vial assembly 580 as the contrast port 556B is coupled to the proximal manifold 555B, rather than the distal manifold 555A which is separated from the proximal manifold 555B by the one-way check valve 553 disposed therebetween.

Figure 6:
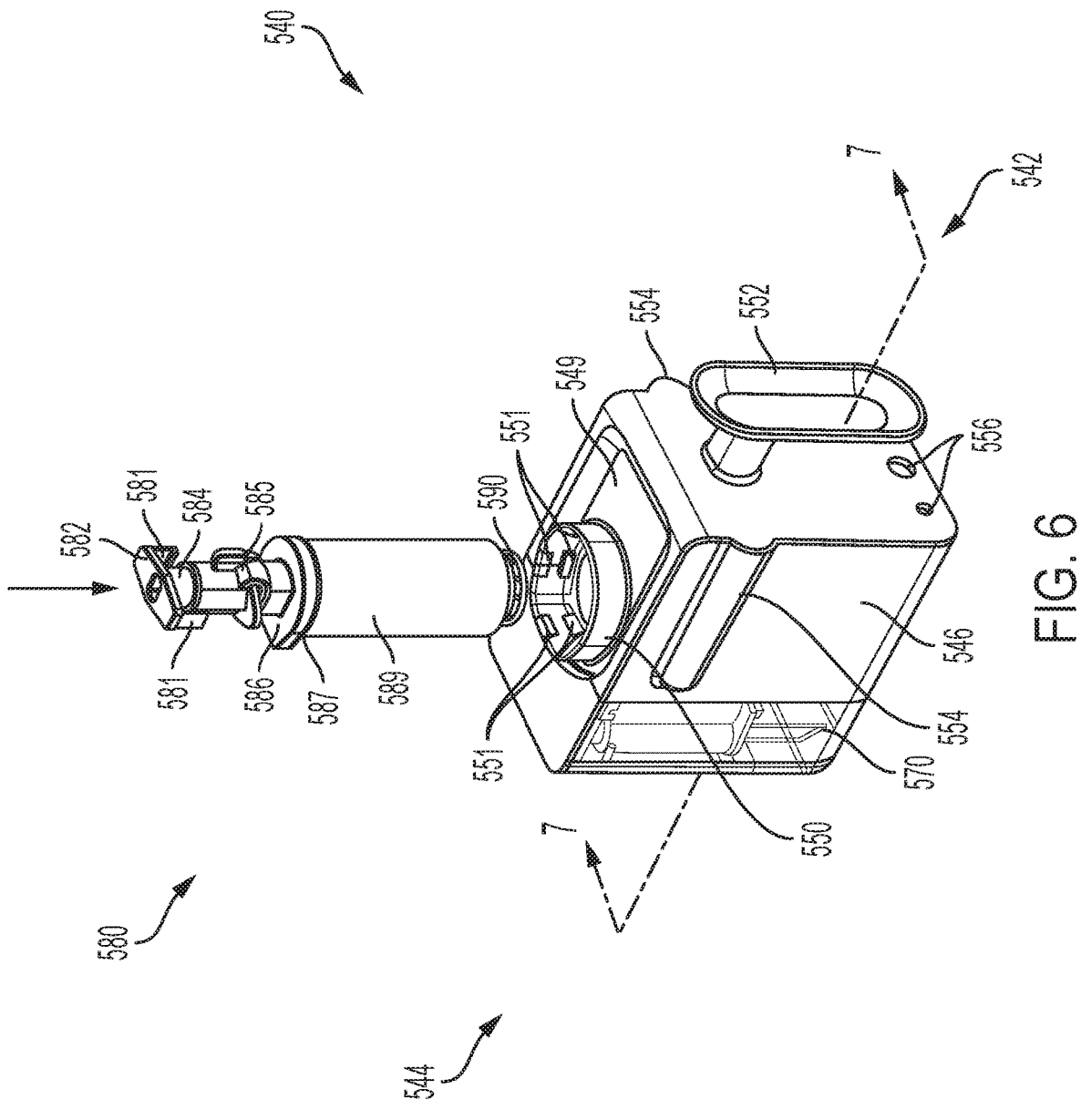
FIG. 6 is a perspective view of the vial sled of FIG. 1 with the vial assembly of FIG. 3 inserted therein according to one or more embodiments shown and described herein.

Referring now to FIG. 6, the vial assembly 580 is slidably inserted into the sled assembly 540. The cap 590 of the vial assembly 580 is inserted through the aperture formed by the locking system 550 at the top surface 548 of the sled assembly 540 and the vial assembly 580 is gradually inserted therethrough until the locking feature 586 contacts the locking system 550.

Figure 7B:
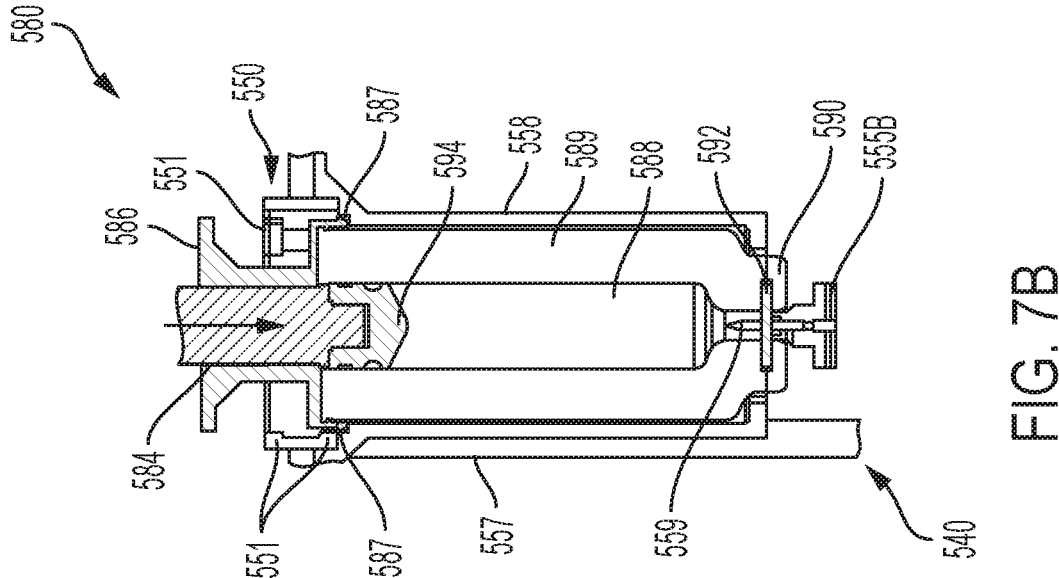
FIG. 7B is a partial cross-sectional view of the vial assembly of FIG. 3 inserted into the vial sled of FIG. 1 at a full locking position, with the cross-section taken along line 7-7 of FIG. 5.
Figure 7A:
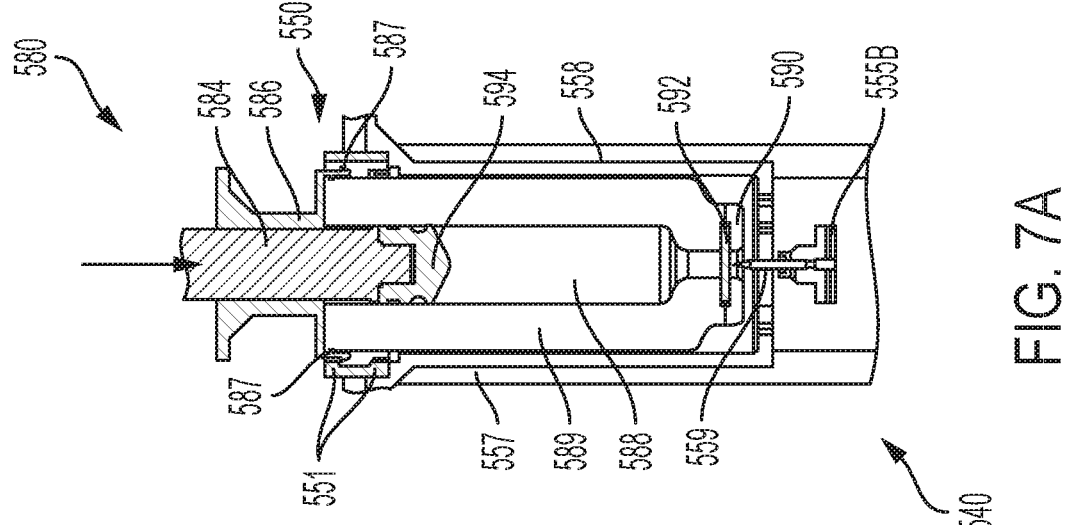
FIG. 7A is a partial cross-sectional view of the vial assembly of FIG. 3 inserted into the vial sled of FIG. 3 at an initial locking position, with the cross-section taken along line 7-7 of FIG. 6.

Referring now to FIG. 7A, the vial assembly 580 is shown disposed within the vial assembly 580, and in particular the vial body 589 is inserted within the vial chamber 558 with the cap 590 positioned proximate to the needle 559. In this instance, the lateral edge 587 of the locking feature 586 encounters a first row of the annular array of projections 551 of the locking system 550. Continued advancement of the vial assembly 580 into the sled assembly 540 causes the annular array of projections 551 positioned along the first row to flex outwardly in response to an application of force generated thereon by the lateral edge 587. In other words, the lateral edge 587 of the locking feature 586 presses outwardly against the annular array of projections 551 in response to the vial assembly 580 being received within the vial chamber 558.

As the annular array of projections 551 of the locking system 550 flex outwardly relative to the lateral edge 587 disposed therein, a continued translation of the vial assembly 580 into the vial chamber 558 causes the lateral edge 587 of the locking feature 586 to advance beyond a first row of the annular array of projections 551 such that the applied-force thereon from the lateral edge 587 is removed. In this instance, the annular array of projections 551 along the first row are permitted to flex inwardly and return to a default position with the lateral edge 587 positioned underneath the first row of projections 551. In some embodiments, a feedback is generated (e.g., an audible click) by the annular array of projections 551 when the lateral edge 587 is extended therethrough to thereby indicate to an operator that the vial assembly 580 is engaged with the locking system 550.

Accordingly, with the first row of projections 551 positioned over the lateral edge 587 of the locking feature 586, the locking system 550 effectively inhibits a withdrawal of the vial assembly 580 from the vial chamber 558 of the sled assembly 540 due to an impediment formed by the first row of projections 551. In this instance, the needle 559 is positioned against and/or received through the cap 590 but is not in contact with the septum 592.

Referring now to FIG. 7B, a continued translation of the vial assembly 580 into the vial chamber 558 of the sled assembly 540 provides for a subsequent engagement between the lateral edge 587 of the locking feature 586 and the locking system 550. In particular, the lateral edge 587 encounters a second row of the annular array of projections 551 of the locking system 550. Continued advancement of the vial assembly 580 into the sled assembly 540 causes the projections 551 positioned along the second row to flex outwardly in response to an application of force generated thereon by the lateral edge 587. As the lateral edge 587 advances past the projections 551, the lateral edge 587 presses outwardly against the projections 551 until the lateral edge 587 of the locking feature 586 advances beyond the second row of projections 551 to achieve a locking position L (FIG. 12D).

In this instance, the applied-force from the lateral edge 587 is removed and the annular array of projections 551 along the second row are permitted to flex inwardly and return to a default position with the lateral edge 587 positioned underneath the second row of projections 551. Accordingly, with the second row of projections 551 positioned over the lateral edge 587 of the locking feature 586, the locking system 550 effectively inhibits a withdrawal of the vial assembly 580 from the vial chamber 558 of the sled assembly 540 due to an impediment formed by the second row of projections 551. In this instance in the locking position L, the needle 559 is positioned against and received through the cap 590 and the septum 592. More particularly, the needle 559 punctures the septum 592 of the vial assembly 580 such that the sled assembly 540 is in fluid communication with the vial body 589 of the vial assembly 580 through the needle 559.

Figure 8:
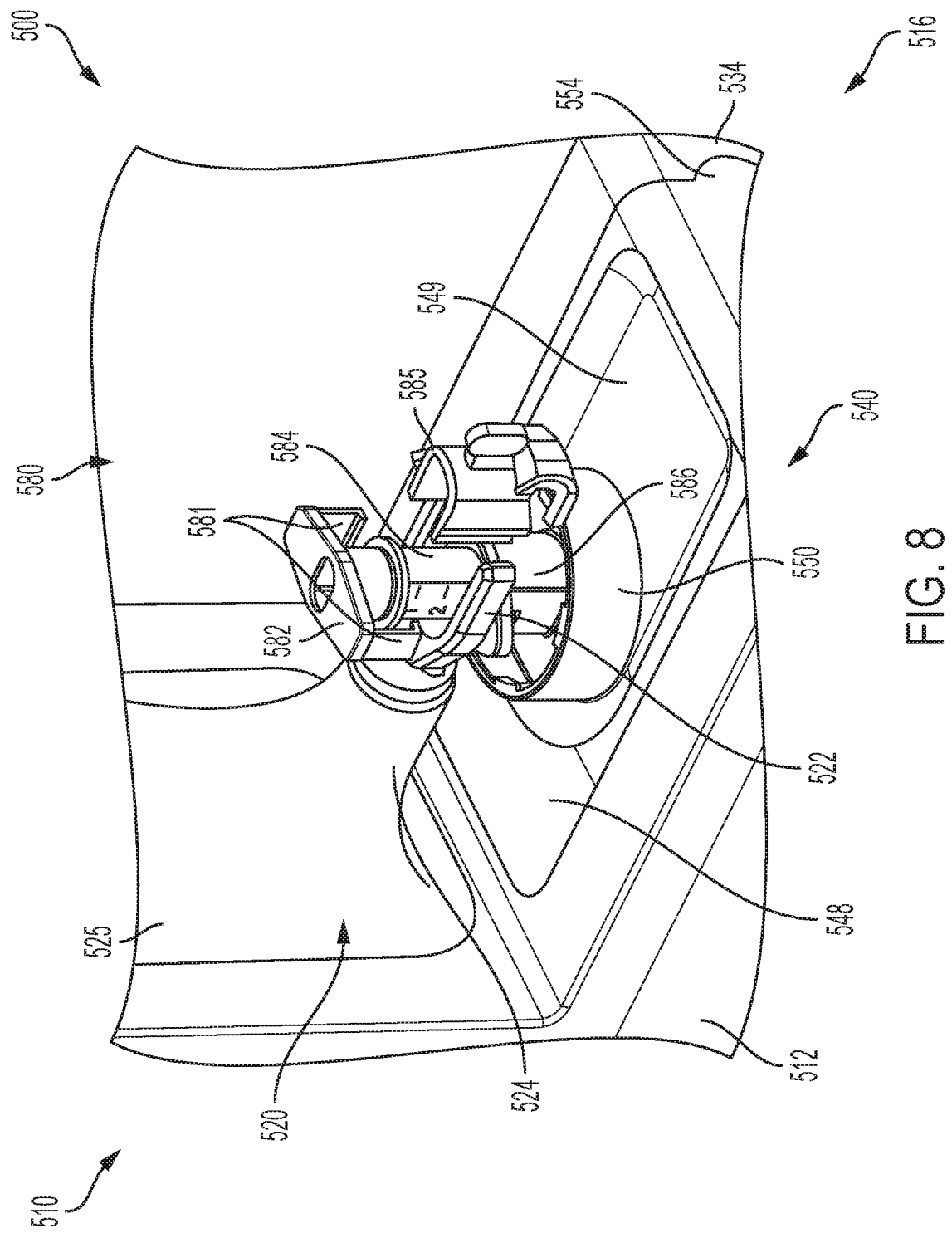
FIG. 8 is a partial-perspective view of the vial sled coupled to the delivery device of FIG. 1 with the lever arm coupled to the vial assembly of FIG. 3 according to one or more embodiments shown and described herein.

Referring now to FIGS. 1 and 8, with the vial assembly 580 securely coupled to the sled assembly 540, the sled assembly 540 is coupled to the console assembly 510 by translating the proximal end 542 of the sled assembly 540 toward and into the distal end 516 of the console assembly 510. In particular, the proximal end 542 of the sled assembly 540 is directed into the sled cavity 532 of the console assembly 510 by aligning the alignment ribs 554 of the sled assembly 540 with the alignment features 534 of the console assembly 510. Once the distal end 544 and the proximal end 542 of the sled assembly 540 are fully seated within the sled cavity 532 of the console assembly 510, the electrical contacts 574 (FIG. 2) of the removable battery pack 570 interact with corresponding electrical contacts 511 (FIG. 1) of the console assembly 510. In this instance, power from the battery 572 is transmitted to the console assembly 510 via the electrical contacts 574, thereby activating the console assembly 510 of the delivery device 500. In this instance, the interface display 530 of the console assembly 510 is activated to display pertinent, real-time information relating to the delivery device 500 during a procedure.

Referring back to FIG. 8, with the distal end 544 of the sled assembly 540 fully seated within the sled cavity 532 and the vial engagement mechanism 520 translated to a lower position, the pair of lever arms 522 engage the safety tab 585 of the vial assembly 580 thereby decoupling the safety tab

585 from the plunger 584. In other words, as the sled assembly 540 is translated into the sled cavity 532 in response to a force applied along the handle 552 at the proximal end 542, a position of the lever arms 522 of the vial engagement mechanism 520 are aligned with and encounter the safety tab 585 of the vial assembly 580. Accordingly, a continued translation of the sled assembly 540 into the sled cavity 532 provides for a disengagement of the safety tab 585 from the plunger 584 by the pair of lever arms 522. In this instance, the plunger 584 of the vial assembly 580 is uninhibited from translating into and/or out of the internal chamber 588 of the vial body 589 in response to an actuation of the vial engagement mechanism 520 coupled thereto.

Figure 9:
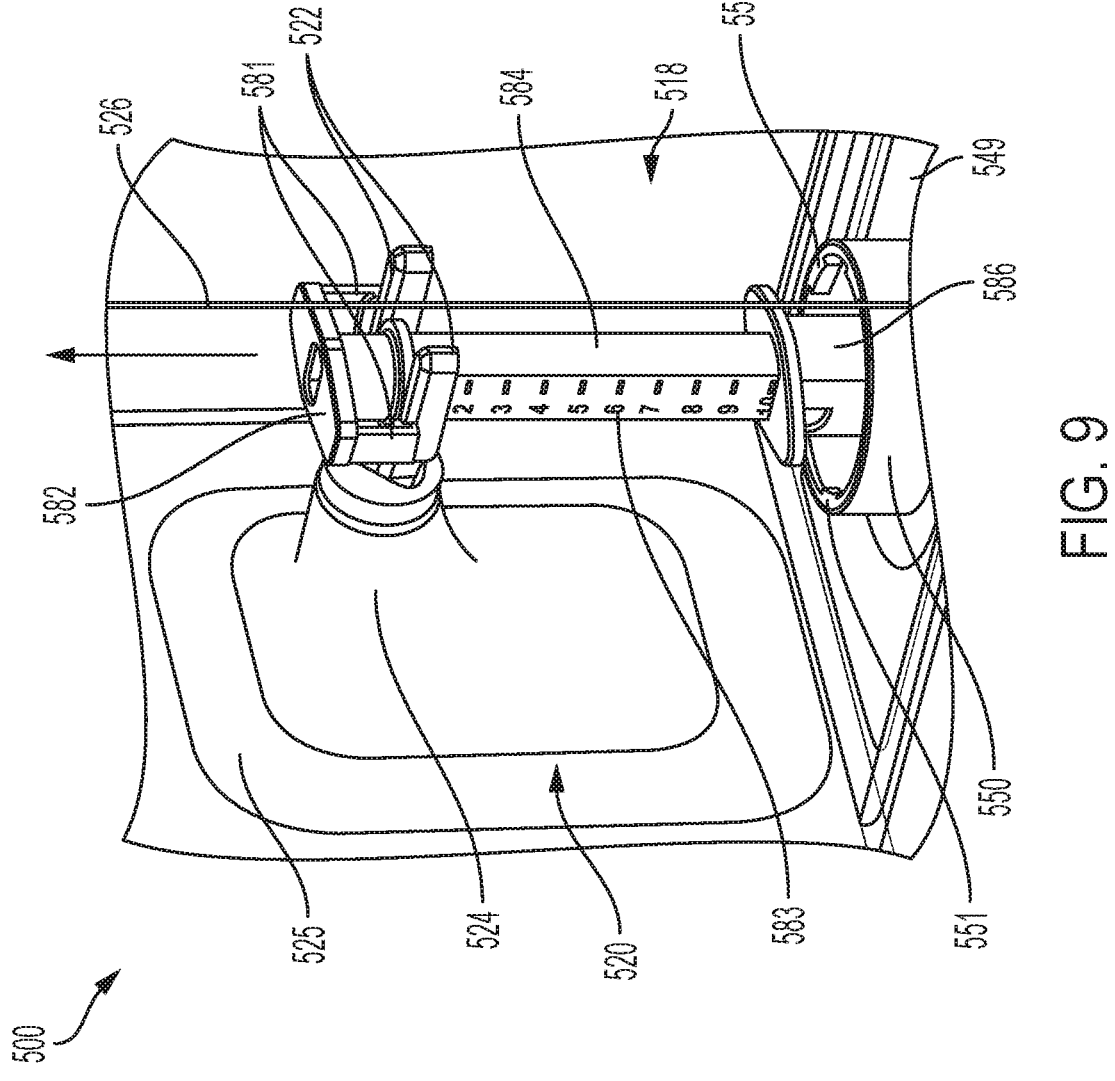
FIG. 9 is a perspective view of the vial sled coupled to the delivery device of FIG. 1, with the lever arm coupled to the vial assembly of FIG. 3 and translated to an extended position according to one or more embodiments shown and described herein.

Referring now to FIG. 9, the handle 528 of the console assembly 510 is actuated (e.g., translated relative downward) to thereby move (e.g., linearly translate) the vial engagement mechanism 520 within the vial containment region 518 distally away from the sled cavity 532 and the sled assembly 540 received therein. In this instance, with the pair of lever arms 522 of the vial engagement mechanism 520 positioned about the plunger 584 of the vial assembly 580, translation of the neck 524 and the pair of lever arms 522 causes the pair of lever arms 522 to engage the engagement head 582, and in particular a bottom end of the pair of arms 581. With a removal of the safety tab 585, the plunger 584 is operable to translate upward and out of the vial body 589 of the vial assembly 580 in response to a translation of the vial engagement mechanism 520. Accordingly, the plunger 584 translates upward simultaneous with the translation of the vial engagement mechanism 520, due to the pair of arms 581 of the engagement head 582 being pulled upwardly by the pair of lever arms 522, in response to an actuation of the handle 528.

In this instance, the pair of lever arms 522 of the vial engagement mechanism 520 is not securely coupled to the pair of arms 581 of the engagement head 582. Rather, the pair of lever arms 522 are merely positioned beneath the pair of arms 581 such that translation of the neck 524 of the vial engagement mechanism 520 causes the pair of lever arms 522 to abut against and pull the pair of arms 581 upward. It should be understood that the annular array of projections 551 of the locking system 550 inhibits a movement and/or an upward translation of the vial assembly 580, and in particular the vial body 589, from the vial chamber 558 of the sled assembly 540 as the vial engagement mechanism 520 pulls the plunger 584 of the vial assembly 580 relatively upward within the vial containment region 518. Additionally, it should further be understood that the alignment features 534 of the console assembly 510 inhibit a movement and/or upward translation of the sled assembly 540 from the sled cavity 532 of the console assembly 510 as the vial engagement mechanism 520 pulls the vial assembly 580 stored within the sled assembly 540 relatively upward within the vial containment region 518.

Still referring to FIG. 9, continued actuation of the handle 528 of the console assembly 510 provides for a continued translation of the vial engagement mechanism 520, and the plunger 584 as a result, until the annular washer 596 encounters the locking feature 586 (See FIG. 4). In this instance, the annular washer 596 inhibits the plunger 584 from translating further relative to the vial body 589 despite a continued actuation of the handle 528 of the console assembly 510. With the annular washer 596 of the vial assembly 580 abutting against the locking feature 586 and thereby inhibiting the plunger 584 from further translating out of the internal chamber 588 of the vial body 589 (and the aperture formed by the locking system 550), continued actuation of the handle 528 causes the pair of arms 581 of the engagement head 582 to flex outwardly relative to the plunger 584 due to an upward force applied thereto by the pair of lever arms 522 in response to the vial engagement mechanism 520 translating upward and the plunger 584 being inhibited from moving further.

In other words, with the pair of lever arms 522 pressed against the pair of arms 581 of the engagement head 582, continued translation of the neck 524 of the vial engagement mechanism 520 causes the pair of lever arms 522 to translate upward thereby applying a force against the pair of arms 581 of the engagement head 582. With the engagement head 582 integrally formed with the plunger 584 and the plunger 584 inhibited from translating further relative to the vial body 589 due to an impediment formed between the annular washer 596 and the locking feature 586, the pair of arms 581 of the engagement head 582 are flexibly deformed to expand outwardly to accommodate an upward translation of the pair of lever arms 522. As a result, the pair of lever arms 522 of the vial engagement mechanism 520 are securely coupled to the pair of arms 581 of the engagement head 582 via a snap-fit engagement, thereby locking the vial engagement mechanism 520 to the vial assembly 580.

Referring again to FIG. 5, as the vial engagement mechanism 520 and the plunger 584 are simultaneously translated within the vial containment region 518, a negative pressure is generated within the internal chamber 588 of the vial body 589 due to a retraction of the stopper 594. In this instance, with the saline bag coupled to the sled assembly 540 via the contrast line 10B and the contrast port 556B, saline from the saline bag is pulled into the internal chamber 588 of the vial body 589 through the proximal manifold 555B and the needle 559. Accordingly, with the vial body 589 being preloaded with a radioactive fluid media (e.g., radioembolizing microspheres), the saline is effectively mixed with the radioactive fluid media within the vial body 589 as the plunger 584 is retracted from the internal chamber 588 and the negative pressure is generated through the delivery device 500.

Figure 10:
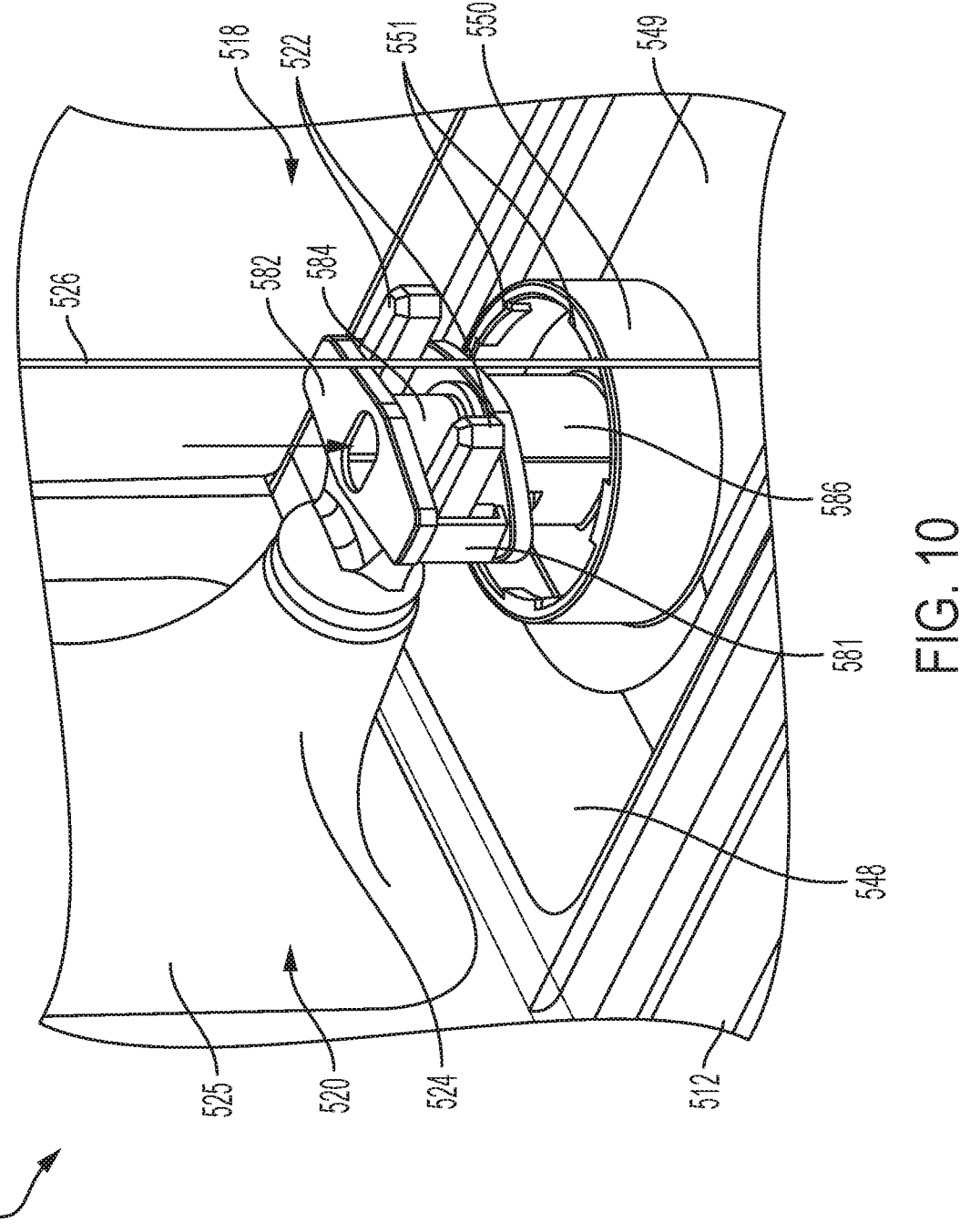
FIG. 10 is a perspective view of the vial sled coupled to the delivery device of FIG. 1, with the lever arm coupled to the vial assembly of FIG. 3 and translated to a lowered position according to one or more embodiments shown and described herein.

Referring now to FIG. 10, actuation of the handle 528 in an opposite direction (e.g., translated and/or pivoted downward relative to the base 512) provides for a simultaneous movement (e.g., linear translation) of the vial engagement mechanism 520. In this instance, the neck 524 translates downward toward the sled cavity 532 thereby causing the plunger 584 to translate into the vial body 589 due to a secured engagement between the pair of arms 581 of the engagement head 582 and the pair of lever arms 522 of the vial engagement mechanism 520. With the stopper 594 movably disposed within the vial body 589, translation of the plunger 584 causes a simultaneous translation of the stopper 594 through the vial body 589 thereby generating a positive pressure therein. As a result, a dose of the saline and radioactive fluid media mixture stored within the internal chamber 588 is transferred outward of the vial body 589 through the needle 559 and into the proximal manifold 555B. With the one-way check valve 553 configured to permit fluid communication from the proximal manifold 555B to the distal manifold 555A, the dose is delivered therethrough and into the dose delivery line 10A via the dose delivery port 556A.

Referring back to FIG. 5, the sled assembly 540 further includes one-way check valves 553A in-line with the contrast line 10B and the flushing line 10C. In particular, the one-way check valves 553A are configured to permit fluid communication from the contrast port 556B and the flushing port 556C into the manifolds 555A, 555B, and further configured to prevent fluid communication from the manifolds 555A, 555B to the contrast port 556B and the flushing port 556C. Accordingly, it should be understood that the dose delivered from the vial body 589 to the manifold 555A, 555B is incapable of being directed into the contrast line 10B or the flushing line 10C due to the one-way check valves 553A positioned therein. Thus, the dose is directed to the dose delivery port 556A and received at the catheter fluidly coupled thereto by the dose delivery line 10A. In other words, the one-way check valves 553A prevent a backflow of fluid into the sled assembly 540 and/or the vial assembly 580 coupled thereto.

II. Vial Assembly Embodiments

As briefly noted above, the delivery device 500 described herein may include a vial assembly 580, embodiments of which are described in greater detail below with respect to FIGS. 11A-17. Referring to FIG. 11A, a vial 600 is shown. The vial includes a vial body 602 disposed between a distal end 604 and a proximal end 606. The distal end 604 includes a top distal surface 608 defining an aperture 609.

Referring to FIG. 11B, the proximal end 606 includes a bottom proximal surface 610. The vial body 602 includes a length 612 disposed between the distal end 604 and the proximal end 606. In an embodiment, the length 612 is 3.295 inches.

Further, the distal end 604 includes a lip thickness 614 of a lip and an edge thickness 616. As shown in the detail view in FIG. 11C of a proximal edge of the distal end 604 with the edge thickness 616, a curvature ledge under the proximal edge includes a radius of curvature 618. In embodiments, a lip edge extending from the top distal surface 608 may extend at a 45 degree angle to arrive at the lip, the lip thickness 614 may be 0.039 inches, and the radius of curvature 618 of the curvature ledge may be 0.020 inches. Referring to FIG. 11D, the distal end 604 including the top distal surface 608 includes a diameter 620. In an embodiment, the diameter 620 may be 1.299 inches.

Referring to FIG. 12A, a cross-sectional view of an embodiment of the vial 600 of FIG. 11A is shown as a vial 600A, with the cross-section taken along line 12A-12B of the vial 600 of FIG. 11B. The vial 600A includes a distal sidewall 622 along the distal end 604 and a proximal sidewall 624 along the proximal end 606. The proximal sidewall 624 defines apertures as one or more fastener mechanisms 626 configured to receive a fastener to hold, for example, a septum 592 to the vial 600A at the proximal end 606. The distal sidewall 622 defines a particulate region 628 inside the vial 600A. The proximal sidewall 624 defines a neck region 630A and a septum region 632 inside the vial 600A. The septum region 632 is configured to hold the septum 592.

The particulate region 628 has a particulate region length 634 co-aligned with a longitudinal axis 636 of the vial 600A. The particulate region 628 and the neck region 630A are connected via a connecting wall that is angled at an angle 638 with respect to the longitudinal axis 636. A first distal portion of the connecting wall has a radius of curvature 640, and a second more distal portion of the connecting wall has a radius of curvature of 642A. In embodiments, the particulate region length 634 is 2.886 inches, the angle 638 is 63 degrees, the radius of curvature 640 is 0.10 inches, and the radius of curvature 642A is 0.08 inches. The aperture 609 of the top distal surface 608 may have a diameter of 0.568 inches plus or minus a range of about 0.002 inches.

In FIG. 12B, the neck region 630A of the vial 600A is shown in more detail. The neck region 630A includes a diameter 644A. The septum region 632 includes an internal diameter 646A, an external diameter 648, a septum region thickness 650, and a septum region radius of curvature 652. In embodiments, the diameter 644A of the neck region 630A is 0.200 inches, the internal diameter 646A of the septum region 632 is 0.264 inches, the external diameter 648 of the septum region 632 is 0.560 inches. The septum region thickness 650 may be 0.035 inches plus or minus a range of 0.002 inches. The radius of curvature 652 may be 0.01 inches.

A further detail view of the septum region 632 in FIG. 12B shows a septum relief area configured to provide relief to the septum 592 in the septum region 632. The septum relief area includes a relief thickness 654 of a connecting relief wall between a first relief wall and a second relief wall, and a relief angle 656 of the connecting relief wall. In embodiments, the relief thickness 654 may be 0.005 inches, and the relief angle 656 may be 30 degrees.

Referring to FIG. 12C, a bottom proximal view of the proximal end 606 of the vial 600A including the proximal surface 610 is shown. The proximal surface 610 defines a fastener spacing diameter 658. In embodiments, the fastener spacing diameter 658 may be 0.939 inches, a through hole is defined by the proximal surface 610 is 0.200 inches to match the diameter 644A of the neck region 630A, and four of the one or more fastener mechanisms 626 may be evenly spaced around the proximal surface 610 and be screws of the type of #6-32 UNC 2*b*. It is contemplated in this and the other embodiments herein that other types of fasteners for use as or by the one or fastener mechanisms 626 as understood to skilled in the art are within the scope of this disclosure.

Referring to FIG. 12D, an embodiment of a vial assembly 580A is shown including the vial 600A of FIG. 12A, a needle 559 disposed in the neck region 630A of the vial 600A in a first position P1, and a mixed fluid 662 in the vial 600A. The needle 559 in this and the other embodiments of the vials 600 described herein includes at least one port 561 configured to inject fluid, such as a saline, to mix with a particulate 660 in the vial 600A to generate the mixed fluid 662 in the particulate region 628 and the neck region 630A. The particulate 660 shown in FIG. 12D and similar vial assembly embodiments shown with mixed fluid 662 herein is representative of of a suspension of particulate 660 after a mixing with the injected fluid to generate the mixed fluid 662. The particulate 660 may be used, for example, as radioactive spheres for radioembolization or as chemoembolization spheres for chemoembolization. While not shown with respect to the vial 600D of FIGS. 15A-15C described below, it is to be understood that the any of the positions of the needle 599 in a vial 600 such as shown in FIGS. 12D-12F may be utilized with any of vials 600 described herein, such as with vials 600B of FIG. 13A, 600C of FIGS. 14A and 14D, 600C1 of FIG. 14E, and 600D of FIG. 15A. The at least one port 561 is further configured to receive the mixed fluid 662 to deliver for a treatment as described herein. In the first position P1, the needle 559 is centrally disposed in the neck region 630A with the at least one needle port 561 facing a sidewall of the neck region 630.

FIG. 12E shows the vial assembly 580A with the needle 599 disposed in the neck region 630A of the vial 600A in a second position P2. In the second position P2, the needle 559 is biased toward a first side closer to a first sidewall and farther from a second sidewall of the neck region 630 with the at least one port 561 facing toward the second sidewall farther from the needle 559. A gap distance between the first side close to the first sidewall and the needle to define the bias may be, for example, 0.5 mm.

FIG. 12F shows the vial assembly 580A with the needle 599 disposed in the neck region 630 of the vial 600A in a third position P3. In the third position P3, the needle 559 is biased toward the first side closer to the first sidewall and farther from the second sidewall of the neck region 630 with the at least one port 561 facing toward the first sidewall closer to the needle 559 and facing away from the second sidewall. A placement of the at least one needle port 561 near a sidewall of the neck region 630 in any of the embodiments of the vials 600 as described herein is configured to permit a turbulent flow and efficient mixing. A gap distance between the first side close to the first sidewall and the needle to define the bias may be, for example, 0.5 mm. The mixed fluid 662 in the vial 600A in each of FIGS. 12D-12F may be the mixed fluid 662 at a time value of 3 seconds (s).

Referring to FIG. 13A, a cross-sectional view of another embodiment of the vial 600 of FIG. 11A is shown as a vial 600B, with the cross-section taken along line 12A-12B of the vial 600 of FIG. 11B. The vial 600B includes a distal sidewall 622 along the distal end 604 and a proximal sidewall 624 along the proximal end 606. The proximal sidewall 624 defines apertures as one or more fastener mechanisms 626 configured to receive a fastener to hold, for example, the septum 592 to the vial 600B at the proximal end 606. The distal sidewall 622 defines a particulate region 628 inside the vial 600B. The proximal sidewall 624 defines a neck region 630B and the septum region 632 inside the vial 600B. The septum region 632 is configured to hold the septum 592.

The particulate region 628 has a particulate region length 634 co-aligned with the longitudinal axis 636 of the vial 600B. The particulate region 628 and the neck region 630B are connected via a connecting wall that is angled at an angle 638 with respect to the longitudinal axis 636. The first distal portion of the connecting wall has the radius of curvature 640, and the second more distal portion of the connecting wall has the radius of curvature of 642B. In embodiments, the particulate region length 634 is 2.886 inches, the angle 638 is 63 degrees, the radius of curvature 640 is 0.10 inches, and the radius of curvature 642A is 0.15 inches. The aperture 609 of the top distal surface 608 may have a diameter of 0.568 inches plus or minus a range of about 0.002 inches.

In FIG. 13B, the neck region 630B of the vial 600B is shown in more detail. The neck region 630B includes a diameter 644B. The septum region 632 includes an internal diameter 646B, an external diameter 648, a septum region thickness 650, and a septum region radius of curvature 652. In embodiments, the diameter 644B of the neck region 630A is 0.118 inches, the internal diameter 646B of the septum region 632 is 0.182 inches, the external diameter 648 of the septum region 632 is 0.560 inches. The septum region thickness 650 may be 0.035 inches plus or minus a range of 0.002 inches. The radius of curvature 652 may be 0.01 inches.

A further detail view of the septum region 632 in FIG. 13B shows a septum relief area configured to provide relief to the septum 592 in the septum region 632. The septum relief area includes a relief thickness 654 of a connecting relief wall between a first relief wall and a second relief wall, and a relief angle 656 of the connecting relief wall. In embodiments, the relief thickness 654 may be 0.005 inches, and the relief angle 656 may be 30 degrees.

Referring to FIG. 13C, a bottom proximal view of the proximal end 606 of the vial 600B including the proximal surface 610 is shown. The proximal surface 610 defines a fastener spacing diameter 658. In embodiments, the fastener spacing diameter 658 may be 0.939 inches, a through hole is defined by the proximal surface 610 is 0.118 inches to match the diameter 644B of the neck region 630B, and four of the one or more fastener mechanisms 626 may be evenly spaced around the proximal surface 610 and be screws of the type of #6-32 UNC 2*b*.

Referring to FIG. 13D, an embodiment of a vial assembly 580 is shown including the vial 600B of FIG. 13A, a needle 559 disposed in the neck region 630B of the vial 600B in the first position P1, and a mixed fluid 662 in the vial 600B. In embodiments, the neck region 630B that is cylindrical may be configured to have a diameter that is close to and slightly larger than a diameter of the needle 559. The mixed fluid 662 in the vial 600B may be the mixed fluid 662 at a time value of 3 seconds (s).

Referring to FIG. 14A, a cross-sectional view of an embodiment of the vial 600 of FIG. 11A is shown as a vial 600C, with the cross-section taken along line 12A-12B of the vial 600 of FIG. 11B. The vial 600C includes a distal sidewall 622 along the distal end 604 and a proximal sidewall 624 along the proximal end 606. The proximal sidewall 624 defines apertures as one or more fastener mechanisms 626 configured to receive a fastener to hold, for example, a septum 592 to the vial 600C at the proximal end 606. The distal sidewall 622 defines a particulate region 628 inside the vial 600C. The proximal sidewall 624 defines a neck region 630D, that includes a conical shape, and a septum region 632 inside the vial 600C. The septum region 632 is configured to hold the septum 592.

The particulate region 628 has a particulate region length 634 co-aligned with a longitudinal axis 636 of the vial 600C. The particulate region 628 and the neck region 630C are connected via a connecting wall that is angled at an angle 638 with respect to the longitudinal axis 636. A first distal portion of the connecting wall has a radius of curvature 640, and a second more distal portion of the connecting wall has a radius of curvature of 642C. In embodiments, the particulate region length 634 is 2.886 inches, the angle 638 is 63 degrees, the radius of curvature 640 is 0.10 inches, and the radius of curvature 642C is 0.06 inches. The aperture 609 of the top distal surface 608 may have a diameter of 0.568 inches plus or minus a range of about 0.002 inches.

In FIG. 14B, the neck region 630C of the vial 600C is shown in more detail. The neck region 630C includes a diameter 644C and a distal cone diameter 670 from which a tapering transition wall 672 proximally extends to taper at an angle 674 with respect to the longitudinal axis 636. The septum region 632 includes an internal diameter 646C, an external diameter 648, a septum region thickness 650, and a septum region radius of curvature 652. In embodiments, the diameter 644C of the neck region 630C is 0.200 inches, the internal diameter 646C of the septum region 632 is 0.324 inches, the external diameter 648 of the septum region 632 is 0.560 inches. The septum region thickness 650 may be 0.035 inches plus or minus a range of 0.002 inches. The radius of curvature 652 may be 0.01 inches. The distal cone diameter 670 may be 0.248 inches, and the tapering transition wall 672 may have a distal radius of curvature of 0.02 inches, and the angle 674 may be 10 degrees. A length 676 between a distal portion and a proximal portion of the tapering transition wall 672 may be 0.266 inches.

Referring to FIG. 14C, a bottom proximal view of the proximal end 606 of the vial 600C including the proximal surface 610 is shown. The proximal surface 610 defines a fastener spacing diameter 658. In embodiments, the fastener spacing diameter 658 may be 0.939 inches, a through hole is defined by the proximal surface 610 is 0.200 inches to match the diameter 644C of the neck region 630C, and four of the one or more fastener mechanisms 626 may be evenly spaced around the proximal surface 610 and be screws of the type of #6-32 UNC 2*b*.

Referring to FIG. 14D, an embodiment of a vial assembly 580 is shown including the vial 600C of FIG. 12A, a needle 559 disposed in the neck region 630C of the vial 600A in a first position P1, and a mixed fluid 662 in the vial 600C. The mixed fluid 662 in the vial 600C may be the mixed fluid 662 at a time value of 3 seconds (s).

Referring to FIG. 14E, another embodiment of a vial assembly 580 is shown including a vial 600C1 having a different conical shape for the neck region 630C1. A needle 559 is disposed in the neck region 630C1 of the vial 600C1 in the first position P1, and a mixed fluid 662 is shown in the vial 600C1. The mixed fluid 662 in the vial 600C1 may be the mixed fluid 662 at a time value of 3 seconds (s).

Referring to FIG. 15A, a cross-sectional view of an embodiment of the vial 600 of FIG. 11A is shown as a vial 600D, with the cross-section taken along line 12A-12B of the vial 600 of FIG. 11B. The vial 600D includes a distal sidewall 622 along the distal end 604 and a proximal sidewall 624 along the proximal end 606. The proximal sidewall 624 defines apertures as one or more fastener mechanisms 626 configured to receive a fastener to hold, for example, a septum 592 to the vial 600D at the proximal end 606. The distal sidewall 622 defines a particulate region 628 inside the vial 600D. The proximal sidewall 624 defines a neck region 630D and a septum region 632 inside the vial 600D. The septum region 632 is configured to hold the septum 592.

The particulate region 628 has a particulate region length 634D co-aligned with a longitudinal axis 636 of the vial 600D. The particulate region 628 and the neck region 630D are connected via a connecting wall that is sloped along an angle 638 with respect to the longitudinal axis 636. A distal portion of the connecting wall has a radius of curvature of 642D. In embodiments, the particulate region length 634D is 3.109 inches, the angle 638 is 63 degrees, and the radius of curvature 642D is 0.08 inches. The aperture 609 of the top distal surface 608 may have a diameter of 0.568 inches plus or minus a range of about 0.002 inches.

In FIG. 15B, the neck region 630D of the vial 600D is shown in more detail. The neck region 630D includes a diameter 644D. The septum region 632 includes an internal diameter 646D, an external diameter 648, a septum region thickness 650, and a septum region radius of curvature 652. In embodiments, the diameter 644D of the neck region 630D is 0.197 inches, the internal diameter 646A of the septum region 632 is 0.261 inches, the external diameter 648 of the septum region 632 is 0.560 inches. The septum region thickness 650 may be 0.035 inches plus or minus a range of 0.002 inches. The radius of curvature 652 may be 0.01 inches.

A further detail view of the septum region 632 in FIG. 15B shows a septum relief area configured to provide relief to the septum 592 in the septum region 632. The septum relief area includes a relief thickness 654 of a connecting relief wall between a first relief wall and a second relief wall, and a relief angle 656 of the connecting relief wall. In embodiments, the relief thickness 654 may be 0.005 inches, and the relief angle 656 may be 30 degrees.

Referring to FIG. 15C, a bottom proximal view of the proximal end 606 of the vial 600D including the proximal surface 610 is shown. The proximal surface 610 defines a fastener spacing diameter 658. In embodiments, the fastener spacing diameter 658 may be 0.939 inches, a through hole is defined by the proximal surface 610 is 0.200 inches to match the diameter 644D of the neck region 630A, and four of the one or more fastener mechanisms 626 may be evenly spaced around the proximal surface 610 and be screws of the type of #6-32 UNC 2*b*.

The vial 600D of FIGS. 15A-15C may be configured as a flat bottom embodiment in which the septum 592 is housed in both the septum region 632 and partially or fully in the neck region 630D. When the septum 592 is housed in both the septum region 632 and fully in the neck region 630D, the at least one port 561 of the needle 559 may be disposed in the particulate region 628 in an embodiment. Alternatively, the septum 592 may be housed in the septum region 632 and not in the neck region 630D.

In the embodiments described herein, the vial assembly 580, 580 includes a vial 600 and a needle 559. In non-limiting examples, the vial assemblies 580, 580A may include vials 600A, 600B, 600C, and 600C1 of FIGS. 12D, 13D, 14D, and 14E in the position P1. Each vial 600 may include a particulate material (e.g., the particulate 660), a septum 592, and a neck region 630 (e.g., neck regions 630A, 630B, 630C, 630C1, and 630D of FIGS. 12A, 13A, 14A, 14E, and 15A) including a first width 644 (e.g., the first width corresponding to the diameters 644A, 644B, 644C, and 644D of FIGS. 12B, 13B, 14B, and 15B), and a particulate region 628 including a second width 609 (e.g., the second width corresponding to the diameter associated with the aperture 609 of FIGS. 12A, 13A, 14A, and 15A) greater than the first width 644.

In embodiments, the second width 609 may be at least two times greater than the first width 644. The septum 592 may be configured to be disposed proximally adjacent to the neck region 630, and the particulate region 628 may be disposed distally adjacent to the neck region 630. The septum 592 may be configured to be disposed in a septum region 632 of the vial 600. The septum region 632 may include a third width (e.g., corresponding to the external diameter 648 of the septum region 632 as described herein) that is greater than the first width 644 of the neck region 630, and the neck region 630 may be disposed between the septum region 632 and the particulate region 628. The septum 592 may be rectangular, and the septum region 632 may include comprises a rectangular configuration sized and shaped to house the septum 592 in an air-tight seal. At least a portion of the neck region 630 may be configured to house at least a portion of the septum 592.

In embodiments, the vial 600 may include an external wall defined by the vial body 602 and including an external wall width (e.g., corresponding to the diameter 620 of the top distal surface 608 of the vial 600 as shown in FIG. 11D), a particulate region thickness between the external wall and the particulate region 628, and a neck region thickness between the external wall and the neck region 630, wherein the neck region thickness is greater than the particulate region thickness. The neck region thickness may be at least 1.5 times or at least 2 times greater than the particulate region thickness. The vial assembly 580, 580A may further include a particulate material assembly, the particulate material assembly comprising a console (e.g., corresponding to the console assembly 510 of FIG. 1) including a vial containment region 518, and the vial engagement mechanism 520 extending from the console within the vial containment region 518, wherein the vial engagement mechanism 520 may be configured to engage the vial assembly

580, 580A and move the vial assembly 580, 580A to the locked position L as described herein.

A connecting wall adjoining the neck region 630 and the particulate region 628 may be angled with respect to a longitudinal axis 636 of the vial 600. The connecting wall may be angled at a 63 degree angle with respect to the longitudinal axis 636. In embodiments, the connecting wall may be angled in a range of from about 20 degrees to about 90 degrees with respect to the longitudinal axis 636. Alternatively, the connecting wall adjoining the neck region 630 and the particulate region 628 may be sloped with respect to the longitudinal axis 636 of the vial 600, such as shown in vial 600D of FIG. 15A. In embodiments, the connecting wall including the sloped configuration may prevent particulate 660 from settling into corners and/or edges of the particulate region 628.

In some embodiments, the neck region 630 may include a cylindrical shape, such as shown in neck regions 630A, 630B, and 630D in FIGS. 12A, 13A, and 15A. The cylindrical shape may include a pair of sidewalls in a cross-section that are parallel with respect to each other and spaced apart at the first width 644. A septum width 648 (e.g., the septum width corresponding to the external diameter 648 of the septum region 632) may be in a range of from about 2.8 times to 3.08 times the first width 644 of the neck region 630. In embodiments, the septum width 648 may be in a range of from about 1.2 times to 10.0 times the first width 644 of the neck region 630.

In some embodiments, the neck region 630 may include a conical shape, such as shown in neck regions 630C, 630C1 in FIGS. 14A, 14D, and 14E. The conical shape may include a pair of sidewalls in a cross-section that taper in a proximal and outward direction with respect to each other, such as shown via the tapering transition wall 672 of FIG. 14B. As shown in the embodiments of FIGS. 14A-14E, the vial 600C, 600C1 may include a particulate material (e.g., the particulate 660), the septum 592, the neck region 630C including a first width 644C and including a conical shape, a particulate region 628 including a second width 609 greater than the first width 644C, and an external wall defined by an external surface of the vial body 602. The external wall may include an external wall width (e.g., corresponding to a diameter of the aperture 609), a particulate region thickness between the external wall and the particulate region 628, and a neck region thickness between the external wall and the neck region 630C. The neck region thickness may be greater than the particulate region thickness. The vial 600C may further be included with a vial assembly 580 and a particulate material assembly to deliver particulate material such as through the delivery device 500 described herein. The vial assembly 580 may include the vial 600C and the needle 559 and may be configured to move the vial 600C to a locked position L. The needle 559 may include at least one port 561 configured to puncture the septum of the vial assembly 580 when the vial assembly 580 is in the locked position L. As shown in FIGS. 14D-14E, the at least one port 561 may be further configured to be in the neck region 630C, 630C1 of the vial assembly 580 when the vial assembly 580 is in the locked position L. The particulate material assembly may include a console (e.g., of the console assembly 510) including a vial containment region 518 and a vial engagement mechanism 520 extending from the console within the vial containment region 518, and the vial engagement mechanism 520 may be configured to engage the vial assembly 580 including the vial 600C and move the vial assembly 580 including the vial 600C to the locked position L as described herein.

The needle may include at least one port 561, as shown in FIGS. 12D-12F, 13D, and 14D-14E. The vial assembly 580, 580A is configured to move to a locked position L (e.g., as shown in the positions P1 of FIGS. 12D, 13D, 14D, and 14E, the position P2 of FIG. 12E, and the position P3 of FIG. 12F). The needle 559 is configured to puncture the septum 592 of the vial assembly 580, 580A when the vial assembly 580, 580A is in the locked position L. The at least one port 561 is further configured to be in the neck region 630 of the vial assembly 580, 580A when the vial assembly 580, 580A is in the locked position L. The at least one port 561 is configured to inject a fluid into the vial assembly 580, 580A to mix with the particulate material upon actuation of a vial engagement mechanism (e.g., the vial engagement mechanism 520 of FIG. 1) in a first direction and to receive a resulting mixed fluid 662 from the vial assembly 580, 580A upon actuation of the vial engagement mechanism 520 in a second direction opposite the first direction.

Examples

The embodiments of the vials 600 described herein, such as described with respect to FIGS. 11A-15C, are configured to reduce and/or minimize isolated volumes of microspheres (e.g., the particulate 660) in the particulate regions 628 and neck regions 630 of the vials 600 while preventing microsphere resuspension and improving flow rates and delivery performance. Flow rates for mixing to inject fluid in the vials 600 as described herein may be 1.0 mL/s for a time period such as 3 s (e.g., 3 s at 1.0 mL/s), or may be other flow rates considered suitable for use with the vials 600, such as 0.3 s at 10.0 mL/s, 0.6 s at 5.0 mL/s, or 1.5 s at 2 mL/s. The simulations of the EXAMPLES of FIGS. 16 and 17 described below utilized parameters of a saline density as the injected fluid of 1000 kg/m$^3$ and a viscosity of 0.001 kg/m-s, and a microspheres density of 1100 kg/m$^3$ and a viscosity of 0.0035 kg/m-s.

In embodiments, a fluid domain of the vial 600 may be set to be 74% filled with microspheres, and an initial volume of the microspheres in the fluid domain may be 1.53 mL of the total fluid domain. Thus, an extrapolation of a current fluid domain may be calculated as shown below. For a fluid domain to be set at 74% filled with microspheres over the 100% of the fluid domain, with an initial volume of the microspheres being set at 1.53 mL, a volume of microspheres can be determined to be 1.132 mL per the equation below, which is 74% times 1.53 mL.

$$\frac{V_{microspheres}}{V_{initial}} = \text{Microspheres \%} \qquad \text{EQUATION 1}$$

For a 10 mL vial 600, a same volume of microspheres in the extrapolation is assumed to spread out in the 10 mL vial volume such that an estimated Volume Fraction is 11.32%, which is 1.132 mL divided by 10 mL. Thus, for a homogenous mixture on the 10 mL vial, a volume fraction of microspheres would be 11.32%. In the simulations of FIGS. 16 and 17, the fluid domain is 3 mL.

FIG. 16 shows a graph 700 of a simulation of an amount of microspheres remaining for an injected volume overtime for the vial assemblies 580, 580A including vials 600A, 600B, 600C, and 600C1 of FIGS. 12D, 13D, 14D, and 14E in the position P1. The amount of microspheres (e.g., the particulate 660) remaining in each of the vials 600A, 600B, 600C, and 600C1 for an injected volume of 1.0 mL/s over 3 s, which generates the mixed solution 662 when mixed with the particulate 660, is shown to decrease from 100% for each of these vials to end in a range of approximately from about 2% to about 10%. An equation that may be utilized for determining an amount of microspheres remaining is set forth below.

$$\text{AmountMicrospheres (\%)} = \qquad \text{EQUATION 2}$$
$$\frac{\text{MicrosphereVolume } @t=0}{\text{MicrosphereVolume } @t=n} *100$$

For example, EQUATION 2, time t may be set to 3.0 seconds (s) as n, such that a microsphere volume and time=0 s is divided by a microsphere volume at time=3.0 s and multiplied by 100 to result in a % of microsphere remaining after 3.0 s.

FIG. 17 shows a graph 800 of a simulation of a volume of microspheres remaining for an injected volume overtime for the vial assemblies 580, 580A including vials 600A, 600B, 600C, and 600C1 of FIGS. 12D, 13D, 14D, and 14E in the position P1. The volume of microspheres (e.g., the particulate 660) remaining in each of the vials 600A, 600B, 600C, and 600C1 for an injected volume of 1.0 mL/s over 3 s, which generates the mixed solution 662 when mixed with the particulate 660, is shown to decrease from an initial volume of approximately 52% in each respective vial to end in a range of approximately from about 22% to about 32%.

Equations that may be utilized for determining a volume of microspheres remaining is based on a volume integration as set forth below.

$$\text{VolumeIntegration} = \int x_{microspheres} * v_{cellvolume} \qquad \text{EQUATION 3}$$

$$\text{VolumeMicrospheres (\%)} = \qquad \text{EQUATION 4}$$
$$\frac{\text{VolumeIntegration}}{\text{TotalVolume}} *100$$

For example, EQUATION 3 determines a volume integration of an amount of particulate 660 in the vial 600 after a mixing and divides it by a total volume in EQUATION 4 to reflect a volume remaining of microspheres after mixing percentage compared to the total volume as a percentage of the total volume.

III. Aspects Listing

Aspect 1. A vial assembly comprising a vial and a needle. The vial comprises a particulate material, a septum, a neck region including a first width, and a particulate region including a second width greater than the first width. The needle comprises at least one port. The vial assembly is configured to move to a locked position. The needle is configured to puncture the septum of the vial assembly when the vial assembly is in the locked position. The at least one port is further configured to be in the neck region of the vial assembly when the vial assembly is in the locked position. The at least one port is configured to inject a fluid into the vial assembly to mix with the particulate material upon actuation of a vial engagement mechanism in a first direction and to receive a resulting mixed fluid from the vial assembly upon actuation of the vial engagement mechanism in a second direction opposite the first direction.

Aspect 2. The vial assembly of Aspect 1, wherein the second width is at least two times greater than the first width.

Aspect 3. The vial assembly of Aspect 1 or Aspect 2, wherein the neck region comprises a cylindrical shape.

Aspect 4. The vial assembly of Aspect 3, wherein the cylindrical shape comprises a pair of sidewalls in a cross-section that are parallel with respect to each other and spaced apart at the first width.

Aspect 5. The vial assembly of Aspect 4, wherein a septum width is in a range of from about 1.2 times to 10.0 times the first width of the neck region.

Aspect 6. The vial assembly of Aspect 1 or Aspect 2, wherein the neck region comprises a conical shape.

Aspect 7. The vial assembly of Aspect 6, wherein the conical shape comprises a pair of sidewalls in a cross-section that taper in a proximal and outward direction with respect to each other.

Aspect 8. The vial assembly of any of Aspect 1 to Aspect 7, wherein a connecting wall adjoining the neck region and the particulate region is angled with respect to a longitudinal axis of the vial.

Aspect 9. The vial assembly of Aspect 8, wherein the connecting wall is angled in a range of from about 20 degrees to about 90 degrees with respect to the longitudinal axis.

Aspect 10. The vial assembly of any of Aspect 1 to Aspect 7, wherein a connecting wall adjoining the neck region and the particulate region is sloped with respect to a longitudinal axis of the vial.

Aspect 11. The vial assembly of any of Aspect 1 to Aspect 10, wherein the septum is configured to be disposed proximally adjacent to the neck region, and the particulate region is disposed distally adjacent to the neck region.

Aspect 12. The vial assembly of Aspect 11, wherein the septum is configured to be disposed in a septum region of the vial assembly, the septum region includes a third width that is greater than the first width, and the neck region is disposed between the septum region and the particulate region.

Aspect 13. The vial assembly of Aspect 12, wherein the septum is rectangular, and the septum region comprises a rectangular configuration sized and shaped to house the septum in an air-tight seal.

Aspect 14. The vial assembly of any of Aspect 1 to Aspect 13, wherein at least a portion of the neck region is configured to house at least a portion of the septum.

Aspect 15. The vial assembly of any of Aspect 1 to Aspect 14, wherein the vial comprises an external wall including an external wall width, a particulate region thickness between the external wall and the particulate region, and a neck region thickness between the external wall and the neck region, wherein the neck region thickness is greater than the particulate region thickness.

Aspect 16. The vial assembly of Aspect 15, wherein the neck region thickness is at least 1.5 times greater than the particulate region thickness.

Aspect 17. The vial assembly of Aspect 15, wherein the neck region thickness is at least 2 times greater than the particulate region thickness.

Aspect 18. The vial assembly of any of Aspect 1 to Aspect 17, further comprising a particulate material assembly, the particulate material assembly comprising a console including a vial containment region, and the vial engagement mechanism extending from the console within the vial containment region, wherein the vial engagement mechanism is configured to engage the vial assembly and move the vial assembly to the locked position.

Aspect 19. A vial comprising a particulate material, a septum, a neck region including a first width, a particulate region including a second width greater than the first width, and an external wall. The neck region comprises a conical shape. The external wall includes an external wall width, a particulate region thickness between the external wall and the particulate region, and a neck region thickness between the external wall and the neck region. The neck region thickness is greater than the particulate region thickness.

Aspect 20. The vial of Aspect 19, further comprising a vial assembly and a particulate material assembly. The vial assembly comprises the vial and a needle. The vial assembly is configured to move the vial to a locked position. The needle comprises at least one port configured to puncture the septum of the vial assembly when the vial assembly is in the locked position. The at least one port is further configured to be in the neck region of the vial assembly when the vial assembly is in the locked position. The particulate material assembly comprises a console including a vial containment region and a vial engagement mechanism extending from the console within the vial containment region. The vial engagement mechanism is configured to engage the vial assembly and move the vial assembly to the locked position.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

For the purposes of describing and defining the present disclosure it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A vial assembly, comprising:
  a vial comprising a particulate material, a septum, a neck region including a first width, and a particulate region including a second width greater than the first width; and
  a needle comprising at least one port;
    wherein the vial assembly is configured to move to a locked position;
    wherein the needle is configured to puncture the septum of the vial assembly when the vial assembly is in the locked position;

wherein the at least one port is further configured to be in the neck region of the vial assembly so as to face a side wall of the neck region when the vial assembly is in the locked position; and wherein the at least one port is configured to inject a fluid into the vial assembly to mix with the particulate material upon actuation of a vial engagement mechanism in a first direction and to receive a resulting mixed fluid from the vial assembly upon actuation of the vial engagement mechanism in a second direction opposite the first direction;

wherein the vial comprises an external wall including (i) a distal sidewall disposed along a plane coaxial with a longitudinal axis of the vial assembly and terminating at a distal end of the vial and (ii) a proximal sidewall disposed along the plane and terminating at a proximal end of the vial, the distal side wall comprising a particulate region thickness between the external wall and the particulate region, and the proximal sidewall comprising a neck region thickness between the external wall and the neck region, wherein the neck region thickness of the proximal sidewall is greater than the particulate region thickness of the distal sidewall.

2. The vial assembly of claim 1, wherein the second width is at least two times greater than the first width.

3. The vial assembly of claim 1, wherein the neck region comprises a cylindrical shape.

4. The vial assembly of claim 3, wherein the cylindrical shape comprises a pair of sidewalls in a cross-section that are parallel with respect to each other and spaced apart at the first width.

5. The vial assembly of claim 4, wherein a septum width is in a range of from about 1.2 times to 10.0 times the first width of the neck region.

6. The vial assembly of claim 1, wherein the neck region comprises a conical shape.

7. The vial assembly of claim 6, wherein the conical shape comprises a pair of sidewalls in a cross-section that taper in a proximal and outward direction with respect to each other.

8. The vial assembly of claim 1, wherein a connecting wall adjoining the neck region and the particulate region is angled with respect to the longitudinal axis of the vial.

9. The vial assembly of claim 8, wherein the connecting wall is angled in a range of from about 20 degrees to about 90 degrees with respect to the longitudinal axis.

10. The vial assembly of claim 1, wherein a connecting wall adjoining the neck region and the particulate region is sloped with respect to the longitudinal axis of the vial.

11. The vial assembly of claim 1, wherein the septum is configured to be disposed proximally adjacent to the neck region, and the particulate region is disposed distally adjacent to the neck region.

12. The vial assembly of claim 11, wherein the vial further comprises a septum region configured to hold the septum and defined in the proximal sidewall, wherein the septum region includes a septum relief area comprising a relief thickness and a relief angle, the relief thickness being of a connecting relief wall between a first relief wall and a second relief wall, the connecting relief wall comprising the relief angle, the septum region includes a third width that is greater than the first width, and the neck region is disposed between the septum region and the particulate region.

13. The vial assembly of claim 12, wherein the septum is rectangular, and the septum region comprises a rectangular configuration sized and shaped to house the septum in an air-tight seal.

14. The vial assembly of claim 1, wherein at least a portion of the neck region is configured to house at least a portion of the septum.

15. The vial assembly of claim 1, wherein the vial comprises the external wall including an external wall width.

16. The vial assembly of claim 15, wherein the neck region thickness is at least 1.5 times greater than the particulate region thickness.

17. The vial assembly of claim 15, wherein the neck region thickness is at least 2 times greater than the particulate region thickness.

18. The vial assembly of claim 1, further comprising a particulate material assembly, the particulate material assembly comprising a console including a vial containment region, and the vial engagement mechanism extending from the console within the vial containment region, wherein the vial engagement mechanism is configured to engage the vial assembly and move the vial assembly to the locked position.

19. A vial comprising:

a particulate material;

a septum;

a neck region including a first width, wherein the neck region comprises a conical shape;

a particulate region including a second width greater than the first width; and an external wall including an external wall width, the external wall including (i) a distal sidewall disposed along a plane coaxial with a longitudinal axis of the vial and terminating at a distal end of the vial and (ii) a proximal sidewall disposed along the plane and terminating at a proximal end of the vial, the distal sidewall comprising a particulate region thickness between the external wall and the particulate region, and the proximal sidewall comprising a neck region thickness between the external wall and the neck region, wherein the neck region thickness of the proximal sidewall is greater than the particulate region thickness of the distal sidewall.

20. The vial of claim 19, further comprising:

a vial assembly, comprising the vial, wherein the vial assembly is configured to move the vial to a locked position, and a needle comprising at least one port configured to puncture the septum of the vial assembly when the vial assembly is in the locked position, wherein the at least one port is further configured to be in the neck region of the vial assembly so as to face a side wall of the neck region when the vial assembly is in the locked position;

a particulate material assembly comprising a console including a vial containment region, and a vial engagement mechanism extending from the console within the vial containment region, wherein the vial engagement mechanism is configured to engage the vial assembly and move the vial assembly to the locked position.

* * * * *